(12) United States Patent
Callaghan

(10) Patent No.: US 8,814,947 B2
(45) Date of Patent: Aug. 26, 2014

(54) DEFORMABLE FLAP CATCH MECHANISM FOR OCCLUDER DEVICE

(75) Inventor: David J. Callaghan, Boston, MA (US)

(73) Assignee: W.L. Gore & Associates, Inc., Flagstaff, AZ (US)

( * ) Notice: Subject to any disclaimer, the term of this patent is extended or adjusted under 35 U.S.C. 154(b) by 1221 days.

(21) Appl. No.: 11/729,637

(22) Filed: Mar. 29, 2007

(65) Prior Publication Data
US 2007/0244517 A1 Oct. 18, 2007

Related U.S. Application Data

(60) Provisional application No. 60/787,988, filed on Mar. 31, 2006.

(51) Int. Cl.
*A61F 2/02* (2006.01)
(52) U.S. Cl.
USPC ........................................................ 623/23.72
(58) Field of Classification Search
CPC ................. A61B 17/0057; A61B 2017/00575; A61B 2017/00862; A61B 2017/00623; A61B 2017/00592; A61B 2017/00619; A61B 2017/00606
USPC ........................................ 623/23.72; 606/213
See application file for complete search history.

(56) References Cited

U.S. PATENT DOCUMENTS

| | | |
|---|---|---|
| 3,294,631 A | 12/1966 | Mancusi |
| 3,824,631 A | 7/1974 | Burstein et al. |
| 3,874,388 A | 4/1975 | King et al. |
| 3,875,648 A | 4/1975 | Bone |
| 3,924,631 A | 12/1975 | Mancusi, Jr. |
| 4,006,747 A | 2/1977 | Kronenthal et al. |
| 4,007,743 A | 2/1977 | Blake |

(Continued)

FOREIGN PATENT DOCUMENTS

| | | |
|---|---|---|
| DE | 9413645 U1 | 10/1994 |
| EP | 0362113 | 4/1990 |

(Continued)

OTHER PUBLICATIONS

Athanasion, T., "Coronary Artery Bypass with the Use of a Magnetic Distal Anastomotic Device: Surgical Technique and Preliminary Experience," The Heart Surgery Forum #2004-1024, 2004, 4 pgs.

(Continued)

*Primary Examiner* — Corrine McDermott
*Assistant Examiner* — Son Dang
(74) *Attorney, Agent, or Firm* — DLA Piper LLP (US)

(57) ABSTRACT

Devices, delivery systems, and delivery techniques for an occlusion device for closure of physical anomalies, such as an atrial septal defect, a patent foramen ovale (PFO), and other septal and vascular defects are described. Specifically, an occluder with a catch member that holds the occluder in the deployed, expanded profile configuration is provided within a delivery sheath. The proximal end of the catch member includes a flap that when positioned proximal to the proximal end of the occluder holds the occluder in the expanded profile configuration. The flap is sized and formed of a material that allows the flap to deform by bending back and forth in axial and radial directions. In certain embodiments, the flap has segments divided by notches. In certain embodiments, deforming the flap in the proximal direction requires a different amount of force than deforming the flap in the distal direction.

10 Claims, 15 Drawing Sheets

(56) References Cited

U.S. PATENT DOCUMENTS

| | | |
|---|---|---|
| 4,149,327 A | 4/1979 | Hammer et al. |
| 4,425,908 A | 1/1984 | Simon |
| 4,610,674 A | 9/1986 | Suzuki et al. |
| 4,626,245 A | 12/1986 | Weinstein |
| 4,696,300 A | 9/1987 | Anderson |
| 4,710,192 A | 12/1987 | Liotta et al. |
| 4,796,612 A * | 1/1989 | Reese ............................ 606/324 |
| 4,836,204 A | 6/1989 | Landymore et al. |
| 4,840,623 A | 6/1989 | Quackenbush |
| 4,902,508 A | 2/1990 | Badylak et al. |
| 4,915,107 A | 4/1990 | Rebuffat et al. |
| 4,917,089 A | 4/1990 | Sideris |
| 4,956,178 A | 9/1990 | Badylak et al. |
| 5,021,059 A | 6/1991 | Kensey et al. |
| 5,037,433 A | 8/1991 | Wilk et al. |
| 5,041,129 A | 8/1991 | Hayhurst et al. |
| 5,078,736 A | 1/1992 | Behl |
| 5,106,913 A | 4/1992 | Yamaguchi et al. |
| 5,108,420 A | 4/1992 | Marks |
| 5,149,327 A | 9/1992 | Oshiyama |
| 5,167,363 A | 12/1992 | Adkinson et al. |
| 5,167,637 A | 12/1992 | Okada et al. |
| 5,171,259 A | 12/1992 | Inoue |
| 5,192,301 A | 3/1993 | Kamiya et al. |
| 5,222,974 A | 6/1993 | Kensey et al. |
| 5,226,879 A | 7/1993 | Ensminger et al. |
| 5,236,440 A | 8/1993 | Hlavacek |
| 5,245,023 A | 9/1993 | Peoples et al. |
| 5,245,080 A | 9/1993 | Aubard et al. |
| 5,250,430 A | 10/1993 | Peoples et al. |
| 5,257,637 A | 11/1993 | El Gazayerli |
| 5,275,826 A | 1/1994 | Badylak et al. |
| 5,282,827 A | 2/1994 | Kensey et al. |
| 5,284,488 A | 2/1994 | Sideris |
| 5,304,184 A | 4/1994 | Hathaway et al. |
| 5,312,341 A | 5/1994 | Turi |
| 5,312,435 A | 5/1994 | Nash et al. |
| 5,316,262 A | 5/1994 | Koebler |
| 5,334,217 A | 8/1994 | Das |
| 5,350,363 A | 9/1994 | Goode et al. |
| 5,350,399 A * | 9/1994 | Erlebacher et al. ............ 606/213 |
| 5,354,308 A | 10/1994 | Simon et al. |
| 5,411,481 A | 5/1995 | Allen et al. |
| 5,413,584 A | 5/1995 | Schulze |
| 5,417,699 A | 5/1995 | Klein et al. |
| 5,425,744 A | 6/1995 | Fagan et al. |
| 5,433,727 A | 7/1995 | Sideris |
| 5,451,235 A | 9/1995 | Lock et al. |
| 5,478,353 A | 12/1995 | Yoon |
| 5,480,353 A | 1/1996 | Garza, Jr. |
| 5,480,424 A | 1/1996 | Cox |
| 5,486,193 A | 1/1996 | Bourne et al. |
| 5,507,811 A | 4/1996 | Koike et al. |
| 5,534,432 A | 7/1996 | Peoples et al. |
| 5,540,712 A | 7/1996 | Kleshinski et al. |
| 5,562,632 A | 10/1996 | Davila et al. |
| 5,577,299 A | 11/1996 | Thompson et al. |
| 5,601,571 A | 2/1997 | Moss |
| 5,618,311 A | 4/1997 | Gryskiewicz |
| 5,620,461 A | 4/1997 | Muijs Van De Moer et al. |
| 5,626,599 A | 5/1997 | Bourne et al. |
| 5,634,936 A | 6/1997 | Linden et al. |
| 5,649,950 A | 7/1997 | Bourne et al. |
| 5,649,959 A | 7/1997 | Hannam et al. |
| 5,663,063 A | 9/1997 | Peoples et al. |
| 5,683,411 A | 11/1997 | Kavteladze et al. |
| 5,690,674 A | 11/1997 | Diaz |
| 5,693,085 A | 12/1997 | Buirge et al. |
| 5,702,421 A | 12/1997 | Scheidt |
| 5,709,707 A | 1/1998 | Lock et al. |
| 5,717,259 A | 2/1998 | Schexnayder |
| 5,720,754 A | 2/1998 | Middleman et al. |
| 5,725,552 A | 3/1998 | Kotula et al. |
| 5,733,294 A | 3/1998 | Forber et al. |
| 5,733,337 A | 3/1998 | Carr, Jr. et al. |
| 5,741,297 A | 4/1998 | Simon |
| 5,776,162 A | 7/1998 | Kleshinski |
| 5,776,183 A | 7/1998 | Kanesaka et al. |
| 5,797,960 A | 8/1998 | Stevens et al. |
| 5,800,516 A | 9/1998 | Fine et al. |
| 5,810,884 A | 9/1998 | Kim |
| 5,823,956 A | 10/1998 | Roth et al. |
| 5,829,447 A | 11/1998 | Stevens et al. |
| 5,853,420 A | 12/1998 | Chevillon et al. |
| 5,853,422 A * | 12/1998 | Huebsch et al. ............... 606/213 |
| 5,855,614 A | 1/1999 | Stevens et al. |
| 5,861,003 A | 1/1999 | Latson et al. |
| 5,865,791 A | 2/1999 | Whayne et al. |
| 5,879,366 A | 3/1999 | Shaw et al. |
| 5,893,856 A | 4/1999 | Jacob et al. |
| 5,902,319 A | 5/1999 | Daley |
| 5,904,703 A | 5/1999 | Gilson |
| 5,919,200 A | 7/1999 | Stambaugh et al. |
| 5,924,424 A | 7/1999 | Stevens et al. |
| 5,928,250 A | 7/1999 | Koike et al. |
| 5,944,738 A | 8/1999 | Amplatz et al. |
| 5,955,110 A | 9/1999 | Patel et al. |
| 5,976,174 A | 11/1999 | Ruiz |
| 5,989,268 A | 11/1999 | Pugsley, Jr. et al. |
| 5,993,475 A | 11/1999 | Lin et al. |
| 5,993,844 A | 11/1999 | Abraham et al. |
| 5,997,575 A | 12/1999 | Whitson et al. |
| 6,010,517 A | 1/2000 | Baccaro |
| 6,024,756 A * | 2/2000 | Huebsch et al. ............... 606/213 |
| 6,030,007 A | 2/2000 | Bassily et al. |
| 6,056,760 A | 5/2000 | Koike et al. |
| 6,071,998 A | 6/2000 | Muller et al. |
| 6,077,291 A | 6/2000 | Das |
| 6,077,880 A | 6/2000 | Castillo et al. |
| 6,079,414 A | 6/2000 | Roth |
| 6,080,182 A | 6/2000 | Shaw et al. |
| 6,096,347 A | 8/2000 | Geddes et al. |
| 6,106,913 A | 8/2000 | Scardino et al. |
| 6,113,609 A | 9/2000 | Adams |
| 6,117,159 A | 9/2000 | Huebsch et al. |
| 6,126,686 A | 10/2000 | Badylak et al. |
| 6,132,438 A | 10/2000 | Fleischman et al. |
| 6,143,037 A | 11/2000 | Goldstein et al. |
| 6,152,144 A | 11/2000 | Lesh et al. |
| 6,165,183 A | 12/2000 | Kuehn et al. |
| 6,165,204 A | 12/2000 | Levinson et al. |
| 6,171,329 B1 | 1/2001 | Shaw et al. |
| 6,174,322 B1 | 1/2001 | Schneidt et al. |
| 6,174,330 B1 | 1/2001 | Stinson |
| 6,187,039 B1 | 2/2001 | Hiles et al. |
| 6,190,353 B1 | 2/2001 | Makower et al. |
| 6,206,895 B1 | 3/2001 | Levinson |
| 6,206,907 B1 | 3/2001 | Marino et al. |
| 6,214,029 B1 | 4/2001 | Thill et al. |
| 6,217,590 B1 | 4/2001 | Levinson |
| 6,221,092 B1 | 4/2001 | Koike et al. |
| 6,227,139 B1 | 5/2001 | Nguyen et al. |
| 6,228,097 B1 | 5/2001 | Levinson et al. |
| 6,231,561 B1 | 5/2001 | Frazier et al. |
| 6,245,080 B1 | 6/2001 | Levinson |
| 6,245,537 B1 | 6/2001 | Williams et al. |
| 6,261,309 B1 | 7/2001 | Urbanski |
| 6,265,333 B1 | 7/2001 | Dzenis et al. |
| 6,270,515 B1 | 8/2001 | Linden et al. |
| 6,277,138 B1 | 8/2001 | Levinson et al. |
| 6,277,139 B1 | 8/2001 | Levinson et al. |
| 6,287,317 B1 | 9/2001 | Makower et al. |
| 6,290,674 B1 | 9/2001 | Roue et al. |
| 6,306,150 B1 | 10/2001 | Levinson |
| 6,306,424 B1 | 10/2001 | Vyakarnam et al. |
| 6,312,446 B1 | 11/2001 | Huebsch et al. |
| 6,316,262 B1 | 11/2001 | Huisman et al. |
| 6,319,263 B1 | 11/2001 | Levinson |
| 6,322,548 B1 | 11/2001 | Payne et al. |
| 6,328,727 B1 | 12/2001 | Frazier et al. |
| 6,334,872 B1 | 1/2002 | Termin et al. |
| 6,342,064 B1 | 1/2002 | Koike et al. |
| 6,344,048 B1 | 2/2002 | Chin et al. |
| 6,344,049 B1 | 2/2002 | Levinson et al. |

(56) References Cited

U.S. PATENT DOCUMENTS

| | | |
|---|---|---|
| 6,346,074 B1 | 2/2002 | Roth |
| 6,348,041 B1 | 2/2002 | Klint et al. |
| 6,352,552 B1 | 3/2002 | Levinson et al. |
| 6,355,052 B1 | 3/2002 | Neuss et al. |
| 6,356,782 B1 | 3/2002 | Sirimanne et al. |
| 6,364,853 B1 | 4/2002 | French et al. |
| 6,371,904 B1 | 4/2002 | Sirimanne et al. |
| 6,375,625 B1 | 4/2002 | French et al. |
| 6,375,671 B1 | 4/2002 | Kobayashi et al. |
| 6,379,342 B1 | 4/2002 | Levinson |
| 6,379,368 B1 | 4/2002 | Corcoran et al. |
| 6,387,104 B1 | 5/2002 | Pugsley, Jr. et al. |
| 6,398,796 B2 | 6/2002 | Levinson |
| 6,402,772 B1 | 6/2002 | Amplatz et al. |
| 6,419,669 B1 | 7/2002 | Frazier et al. |
| 6,426,145 B1 | 7/2002 | Moroni |
| 6,436,088 B2 | 8/2002 | Frazier et al. |
| 6,440,152 B1 | 8/2002 | Gainor et al. |
| 6,460,749 B1 | 10/2002 | Levinson et al. |
| 6,482,224 B1 | 11/2002 | Michler et al. |
| 6,488,706 B1 | 12/2002 | Solymar et al. |
| 6,494,888 B1 | 12/2002 | Laufer et al. |
| 6,508,828 B1 | 1/2003 | Akerfeldt et al. |
| 6,514,515 B1 | 2/2003 | Williams |
| 6,548,569 B1 | 4/2003 | Williams et al. |
| 6,551,303 B1 | 4/2003 | Van Tassel et al. |
| 6,551,344 B2 | 4/2003 | Thill |
| 6,585,755 B2 | 7/2003 | Jackson et al. |
| 6,596,013 B2 | 7/2003 | Yang et al. |
| 6,599,448 B1 | 7/2003 | Ehrhard, Jr. et al. |
| 6,610,764 B1 | 8/2003 | Martin et al. |
| 6,623,508 B2 | 9/2003 | Shaw et al. |
| 6,623,518 B2 | 9/2003 | Thompson et al. |
| 6,626,936 B2 | 9/2003 | Stinson |
| 6,629,901 B2 | 10/2003 | Huang |
| 6,666,861 B1 | 12/2003 | Grabek |
| 6,669,722 B2 | 12/2003 | Chen et al. |
| 6,689,589 B2 | 2/2004 | Huisman et al. |
| 6,712,804 B2 | 3/2004 | Roue et al. |
| 6,712,836 B1 | 3/2004 | Berg et al. |
| 6,726,696 B1 | 4/2004 | Houser et al. |
| 6,828,357 B1 | 12/2004 | Martin et al. |
| 6,838,493 B2 | 1/2005 | Williams et al. |
| 6,867,247 B2 | 3/2005 | Williams et al. |
| 6,867,248 B1 | 3/2005 | Martin et al. |
| 6,867,249 B2 | 3/2005 | Lee et al. |
| 6,921,410 B2 | 7/2005 | Porter |
| 2001/0010481 A1 | 8/2001 | Blanc et al. |
| 2001/0014800 A1 | 8/2001 | Frazier et al. |
| 2001/0034537 A1 | 10/2001 | Shaw et al. |
| 2001/0034567 A1 | 10/2001 | Allen et al. |
| 2001/0037129 A1 | 11/2001 | Thill |
| 2001/0039435 A1 | 11/2001 | Roue et al. |
| 2001/0041914 A1 | 11/2001 | Frazier et al. |
| 2001/0041915 A1 | 11/2001 | Roue et al. |
| 2001/0044639 A1 | 11/2001 | Levinson |
| 2001/0049492 A1 | 12/2001 | Frazier et al. |
| 2002/0010481 A1 | 1/2002 | Jayaraman |
| 2002/0019648 A1 | 2/2002 | Akerfeldt et al. |
| 2002/0026208 A1 | 2/2002 | Roe et al. |
| 2002/0029048 A1 | 3/2002 | Miller |
| 2002/0032459 A1 | 3/2002 | Horzewski et al. |
| 2002/0032462 A1 | 3/2002 | Houser et al. |
| 2002/0034259 A1 | 3/2002 | Tada |
| 2002/0035374 A1 | 3/2002 | Borillo et al. |
| 2002/0043307 A1 | 4/2002 | Ishida et al. |
| 2002/0052572 A1 | 5/2002 | Franco et al. |
| 2002/0058989 A1 | 5/2002 | Chen et al. |
| 2002/0077555 A1 | 6/2002 | Schwartz |
| 2002/0095174 A1 | 7/2002 | Tsugita et al. |
| 2002/0096183 A1 | 7/2002 | Stevens et al. |
| 2002/0099389 A1 | 7/2002 | Michler et al. |
| 2002/0107531 A1 | 8/2002 | Schreck et al. |
| 2002/0111537 A1 | 8/2002 | Taylor et al. |
| 2002/0111637 A1 | 8/2002 | Kaplan et al. |
| 2002/0111647 A1 | 8/2002 | Khairkhahan et al. |
| 2002/0120323 A1 | 8/2002 | Thompson et al. |
| 2002/0128680 A1 | 9/2002 | Pavlovic |
| 2002/0129819 A1 | 9/2002 | Feldman et al. |
| 2002/0164729 A1 | 11/2002 | Skraly et al. |
| 2002/0169377 A1 | 11/2002 | Khairkhahan et al. |
| 2002/0183786 A1 | 12/2002 | Girton |
| 2002/0183787 A1 | 12/2002 | Wahr et al. |
| 2002/0183823 A1 | 12/2002 | Pappu |
| 2002/0198563 A1 | 12/2002 | Gainor et al. |
| 2003/0004533 A1 | 1/2003 | Dieck et al. |
| 2003/0023266 A1 | 1/2003 | Welch et al. |
| 2003/0028213 A1 | 2/2003 | Thill et al. |
| 2003/0045893 A1 | 3/2003 | Ginn |
| 2003/0050665 A1 | 3/2003 | Ginn |
| 2003/0055455 A1 | 3/2003 | Yang et al. |
| 2003/0057156 A1 | 3/2003 | Peterson et al. |
| 2003/0065379 A1 | 4/2003 | Babbas et al. |
| 2003/0100920 A1 | 5/2003 | Akin et al. |
| 2003/0120337 A1 | 6/2003 | Van Tassel et al. |
| 2003/0139819 A1* | 7/2003 | Beer et al. ................. 623/23.71 |
| 2003/0171774 A1 | 9/2003 | Freudenthal et al. |
| 2003/0191495 A1 | 10/2003 | Ryan et al. |
| 2003/0195530 A1 | 10/2003 | Thill |
| 2003/0204203 A1 | 10/2003 | Khairkhahan et al. |
| 2004/0044361 A1 | 3/2004 | Frazier et al. |
| 2004/0073242 A1 | 4/2004 | Chanduszko |
| 2004/0176799 A1 | 9/2004 | Chanduszko et al. |
| 2004/0210301 A1 | 10/2004 | Obermiller |
| 2004/0234567 A1 | 11/2004 | Dawson |
| 2005/0025809 A1 | 2/2005 | Hasirci et al. |
| 2005/0043759 A1* | 2/2005 | Chanduszko ................ 606/213 |
| 2005/0113868 A1 | 5/2005 | Devellian et al. |
| 2005/0267523 A1* | 12/2005 | Devellian et al. ............ 606/213 |
| 2005/0273135 A1* | 12/2005 | Chanduszko et al. ........ 606/213 |
| 2005/0288786 A1* | 12/2005 | Chanduszko ............... 623/11.11 |
| 2006/0122647 A1* | 6/2006 | Callaghan et al. ............ 606/213 |
| 2006/0265004 A1 | 11/2006 | Callaghan et al. |
| 2007/0010851 A1 | 1/2007 | Chanduszko et al. |
| 2007/0129755 A1* | 6/2007 | Abbott et al. ................. 606/213 |
| 2007/0167981 A1 | 7/2007 | Opolski |

FOREIGN PATENT DOCUMENTS

| | | |
|---|---|---|
| EP | 0474887 A1 | 3/1992 |
| EP | 0 839 549 | 5/1998 |
| EP | 1013227 A2 | 6/2000 |
| EP | 1046375 A1 | 10/2000 |
| EP | 1222897 A2 | 7/2002 |
| WO | WO-96/25179 | 8/1996 |
| WO | WO-96/31157 | 10/1996 |
| WO | WO-98/07375 | 2/1998 |
| WO | WO-98/08462 | 3/1998 |
| WO | WO-98/16174 | 4/1998 |
| WO | WO-98/29026 | 7/1998 |
| WO | WO-98/51812 | 11/1998 |
| WO | WO-99/05977 | 2/1999 |
| WO | WO-99/18862 | 4/1999 |
| WO | WO 99/18864 | 4/1999 |
| WO | WO-99/18864 | 4/1999 |
| WO | WO-99/18870 | 4/1999 |
| WO | WO-99/18871 | 4/1999 |
| WO | WO-99/30640 | 6/1999 |
| WO | WO-00/27292 | 5/2000 |
| WO | WO-00/44428 | 8/2000 |
| WO | WO-01/21247 | 3/2001 |
| WO | WO-01/30268 | 5/2001 |
| WO | WO-01/49185 | 7/2001 |
| WO | WO-01/78596 | 10/2001 |
| WO | WO-02/17809 | 3/2002 |
| WO | WO-02/24106 | 3/2002 |
| WO | WO-03/024337 | 3/2003 |
| WO | WO-03/053493 | 7/2003 |
| WO | WO-03/059152 | 7/2003 |
| WO | WO-03/063732 | 8/2003 |
| WO | WO-03/077733 | 9/2003 |
| WO | WO-03/082076 | 10/2003 |
| WO | WO-03/103476 | 12/2003 |
| WO | WO-2004/032993 | 4/2004 |

(56) References Cited

FOREIGN PATENT DOCUMENTS

| WO | WO-2004/037333 | 5/2004 |
|---|---|---|
| WO | WO-2004/043266 | 5/2004 |
| WO | WO-2004/043508 | 5/2004 |
| WO | WO-2004/052213 | 6/2004 |
| WO | WO-2005/006990 | 1/2005 |
| WO | WO-2005/018728 | 3/2005 |
| WO | WO-2005/027752 | 3/2005 |
| WO | WO-2005/074813 | 8/2005 |
| WO | WO-2005/092203 | 10/2005 |
| WO | WO-2005/110240 | 11/2005 |
| WO | WO-2005/112779 | 12/2005 |
| WO | WO-2006/036837 | 4/2006 |
| WO | WO-2006/102213 | 9/2006 |

OTHER PUBLICATIONS

Bachthaler, M. et al., "Corrosion of Tungsten Coils After Peripheral Vascular Embolization Theraphy: Influence on Outcome and Tungsten Load", *Catherization and Cardiovascular Interventions,* vol. 62, pp. 380-384, 2004.

European Examination Report, European Application No. 04781644.2, mailed Aug. 23, 2007 (3 Pages).

Falk, V., "Facilitated Endoscopic Beating Heart Coronary Artery Bypass Grafting Using a Magentic Coupling Device," Journal of Thoracic and Cardiovascular Surgery, vol. 126,(5), pp. 1575-1579.

Filsoufi, F., et al., "Automated Distal Coronary Bypass with a Novel Magnetic Coupler (MVP system)," J. Thoracic and Cardiovascular Surgery, vol. 127(1), pp. 185-192.

International Search Report for International Patent Application No. PCT/AU03/00759, filed Jun. 19, 2003.

International Search Report, International Application No. PCT/US02/40850 mailed Jun. 19, 2003 (4 pgs).

International Search Report, International Application No. PCT/US03/01050, mailed Jul. 8, 2003 (1 pg).

International Search Report, International Application No. PCT/US03/09051, mailed Sep. 29, 2003 (2 pgs).

International Search Report, International Application No. PCT/US03/17390, mailed Oct. 6, 2003 (42 pgs).

International Search Report, International Application No. PCT/US03/17715, mailed Mar. 24, 2004 (2 pgs).

International Search Report, International Application No. PCT/US03/32133, mailed Apr. 22, 2004 (1 pg).

International Search Report, International Application No. PCT/US03/34003 mailed Oct. 3, 2004 (4 pgs).

International Search Report, International Application No. PCT/US03/35479, mailed Apr. 14, 2004 (2 pgs).

International Search Report, International Application No. PCT/US03/35998 mailed Jun. 16, 2004 (4 pgs).

International Search Report, International Application No. PCT/US03/39253, mailed Apr. 19, 2004 (4 pgs).

International Search Report, International Application No. PCT/US04/022643, mailed Mar. 31, 2005 (2 pgs).

International Search Report, International Application No. PCT/US04/026998, mailed Apr. 22, 2005 (5 pgs).

International Search Report, International Application No. PCT/US04/029978, mailed Jan. 26, 2005 (3 pgs).

International Search Report, International Application No. PCT/US05/006703, mailed Jul. 25, 2005 (3 pgs).

International Search Report, International Application No. PCT/US05/013705 mailed Aug. 4, 2005 (4 pgs).

International Search Report, International Application No. PCT/US05/015382, mailed Oct. 6, 2005 (4 pgs).

International Search Report, International Application No. PCT/US05/34276, mailed Oct. 9, 2007. (1 pg).

International Search Report, International Application No. PCT/US06/009978, mailed Jul. 13, 2006 (2 pgs).

International Search Report, International Application No. PCT/US07/065546, mailed Oct. 29, 2007. 4 pages.

International Search Report, International Application No. PCT/US2007/065526, mailed Aug. 8, 2007 (4 pgs).

International Search Report, International Application No. PCT/US2007/065541, mailed Aug. 7, 2007 (4 pgs).

International Search Report, International Application No. PCT/US97/14822, mailed Feb. 20, 1998 (2 pgs).

International Search Report, International Application No. PCT/US97/17927, mailed Feb. 10, 1998 (1 pg).

Isotalo, T. et al., "Biocompatibility Testing of a New Bioabsorbable X-Ray Positive SR-PLA 96/4 Urethral Stent", *The Journal of Urology,* vol. 163, pp. 1764-1767, Nov. 1999.

Kimura, A., et al., "Effects of Neutron Irradiation on the Transformation Behavior in Ti—Ni Alloys," Abstract, Proceedings of the Int'l Conf. on Mariensitic Transformations, 1992, pp. 935-940.

Klima, U., "Magnetic Vascular Port in Minimally Invasive Direct Coronary Artery Bypass Grafting," Circulation, 2004, II-55-II-60.

Meier, MD, Bernhard et al., "Contemporary Management of Patent Foramen Ovale," American Heart Association, Inc., Circulation, 2003, vol. 107, pp. 5-9.

Nat'l Aeronautics and Space Administration, "55-Nitinol—The Alloy with a Memory: Its Physical Metallurgy, Properties and Applications," NASA Report, pp. 24-25.

Parviainen, M. et al., "A New Biodegradable Stent for the Pancreaticojejunal Anastomosis After Pancreaticoduodenal Resection: In Vitro Examination and Pilot Experiences in Humans", *Pancreas,* vol. 21, No. 1, pp. 14-21, 2000.

Ramanathan, G., et al., "Experimental and Computational Methods for Shape Memory Alloys," 15th ASCE Engineering Mechanics Conference, Jun. 2-5, 2002.

Ruddy, A.C. et al., "Rheological, Mechanical and Thermal Behaviour of Radipaque Filled Polymers", *Polymer Processing Research Centre, School of Chemical Engineering, Queen's University of Belfast* , 5 pages.

Ruiz, et al, "The Puncture Technique: A New Method for Transcatheter Closure of Patent Foramen Ovale," Catheterization and Cardiovascular Interventions, 2001, vol. 53, pp. 369-372.

Shabalovskaya, S., "Surface, Corrosion amd Biocompatibility Aspects of Nitinol as and Implant Material," Bio-Medical Materials and Engineering, 2002, vol. 12, pp. 69-109.

SMST-2000, "Proceedings of the International Conference on Shape Memory and Superelastic Technologies," Apr. 30 To May 4, 2000, Asilomar Conference Center.

Stockel, "Nitinol Medical Devices and Implants," SMST-2000 Conference Proceedings, 2001, pp. 531-541.

Uchil, J., "Shape Memory Alloys—Characterization Techniques," Pramana—Journal of Physics, 2002, vol. 58(5)(6), pp. 1131-1139.

Vaajanen, A. et al., "Expansion and Fixation Properties of a New Braided Biodegradable Urethral Stent: An Experimental Study in the Rabbit", *The Journal of Urology,* vol. 169, pp. 1771-1174, Mar. 2003.

* cited by examiner

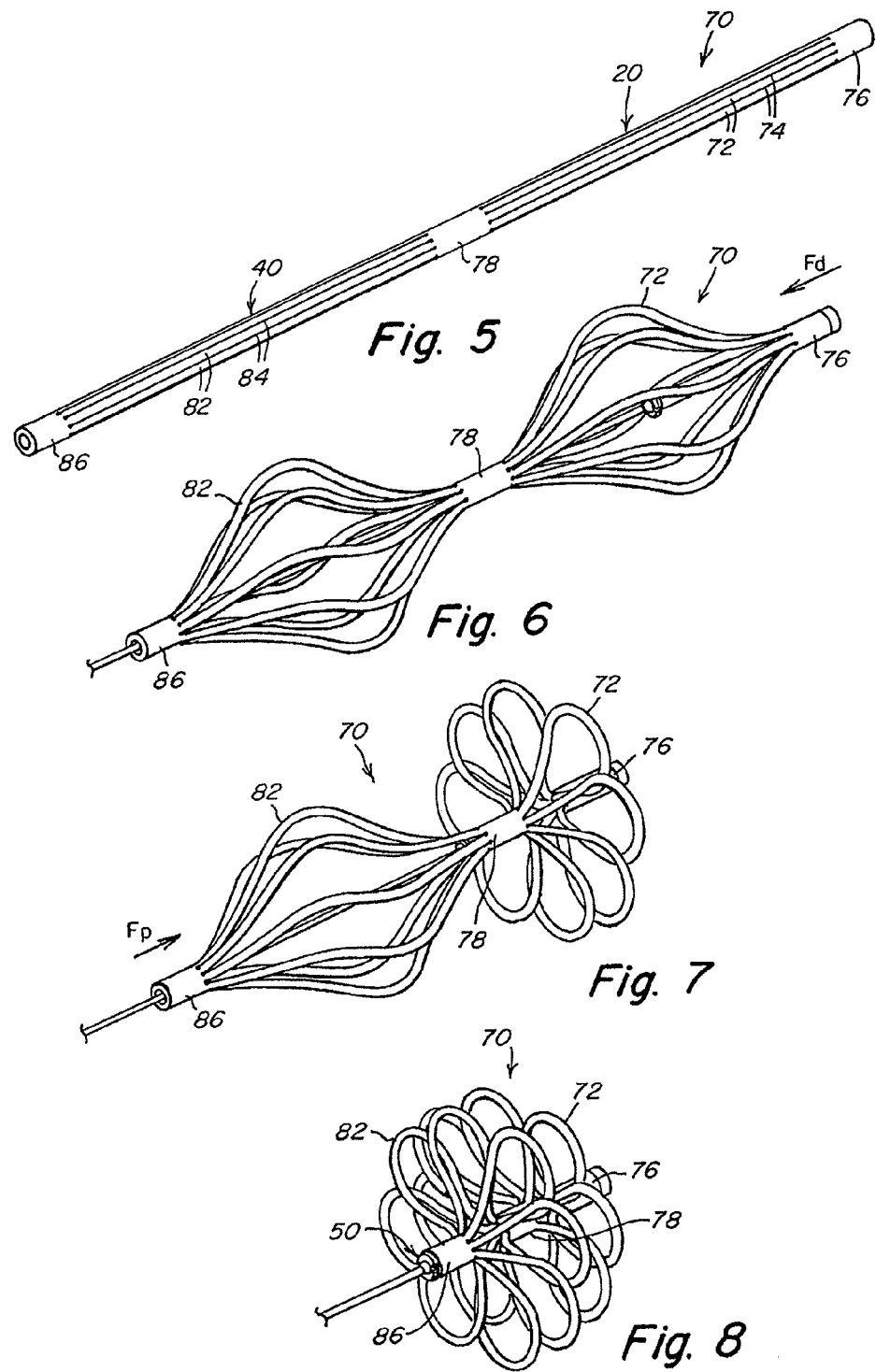

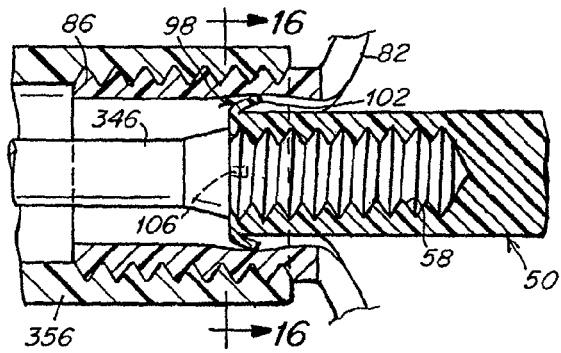
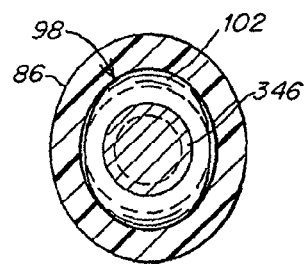
Fig. 15   Fig. 16
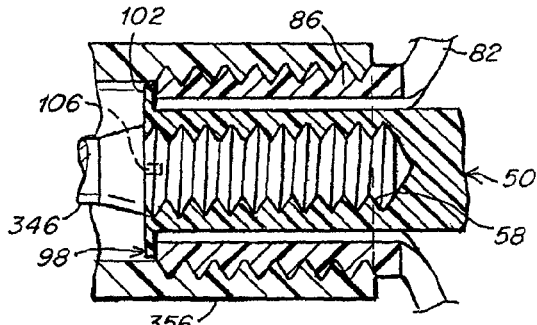
Fig. 17
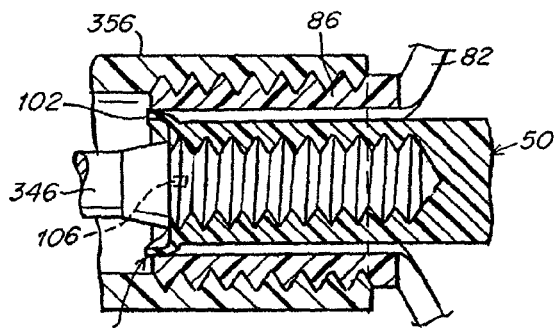
Fig. 18A
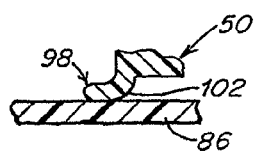
Fig. 18B

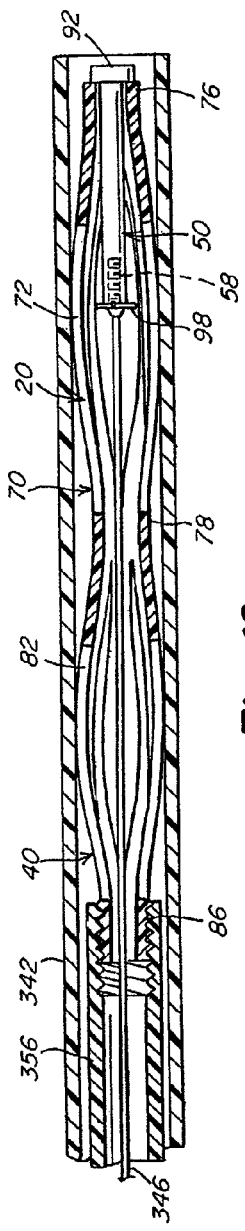
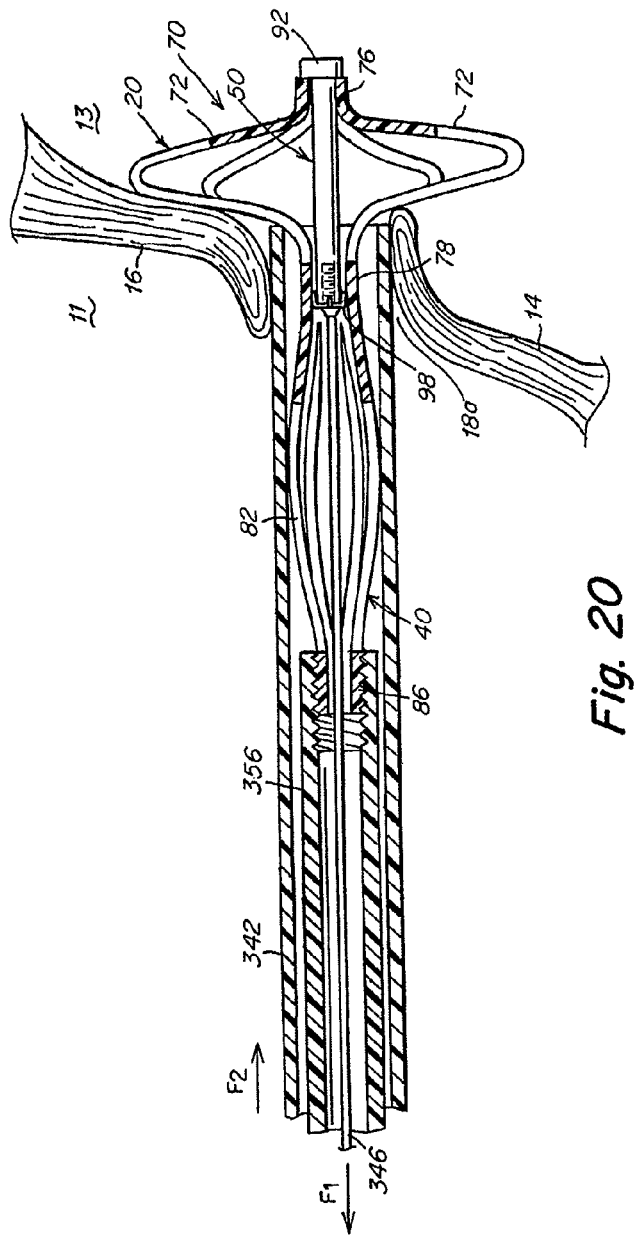
Fig. 19
Fig. 20

DEFORMABLE FLAP CATCH MECHANISM FOR OCCLUDER DEVICE

CROSS-REFERENCE TO RELATED APPLICATIONS

This Application claims the benefit under 35 U.S.C. 119(e) of U.S. Provisional Application No. 60/787,988, filed on Mar. 31, 2006, which is incorporated by reference herein in its entirety.

FIELD OF THE INVENTION

This invention relates generally to occlusion devices for the closure of physical anomalies, such as an atrial septal defect, a patent foramen ovale, and other septal and vascular defects. In particular, this invention relates to a catch mechanism to maintain the occluder in the deployed configuration. The invention also relates to delivery systems and mechanisms for such devices.

BACKGROUND OF THE INVENTION

A patent foramen ovale (PFO), illustrated in FIG. 1, is a persistent, one-way, usually flap-like opening in the wall between the right atrium 11 and left atrium 13 of the heart 10. Because left atrial (LA) pressure is normally higher than right atrial (RA) pressure, the flap usually stays closed. Under certain conditions, however, right atrial pressure can exceed left atrial pressure, creating the possibility that blood could pass from the right atrium 11 to the left atrium 13 and blood clots could enter the systemic circulation. It is desirable that this circumstance be eliminated.

The foramen ovale serves a desired purpose when a fetus is gestating. Because blood is oxygenated through the umbilical cord, and not through the developing lungs, the circulatory system of the fetal heart allows the blood to flow through the foramen ovale as a physiologic conduit for right-to-left shunting. After birth, with the establishment of pulmonary circulation, the increased left atrial blood flow and pressure results in functional closure of the foramen ovale. This functional closure is subsequently followed by anatomical closure of the two overlapping layers of tissue: septum primum 14 and septum secundum 16. However, a PFO has been shown to persist in a number of adults.

The presence of a PFO is generally considered to have no therapeutic consequence in otherwise healthy adults. Paradoxical embolism via a PFO is considered in the diagnosis for patients who have suffered a stroke or transient ischemic attack (TIA) in the presence of a PFO and without another identified cause of ischemic stroke. While there is currently no definitive proof of a cause-effect relationship, many studies have confirmed a strong association between the presence of a PFO and the risk for paradoxical embolism or stroke. In addition, there is significant evidence that patients with a PFO who have had a cerebral vascular event are at increased risk for future, recurrent cerebrovascular events. Another condition, chronic migraine headache, has also been linked to the presence of a PFO. Although researchers are still working on finding an explanation, PFO closure has been shown to eliminate or significantly reduce migraine headaches in many patients.

In certain cases, such as when anticoagulation is contraindicated, surgery may be necessary or desirable to close a PFO. The surgery would typically include suturing a PFO closed by attaching septum secundum to septum primum. This sutured attachment can be accomplished using either an interrupted or a continuous stitch and is a common way a surgeon shuts a PFO under direct visualization.

Umbrella devices and a variety of other similar mechanical closure devices, developed initially for percutaneous closure of atrial septal defects (ASDs), have been used in some instances to close PFOs. These devices potentially allow patients to avoid the side effects often associated with anticoagulation therapies and the risks of invasive surgery. However, umbrella devices and the like that are designed for ASDs are not optimally suited for use as PFO closure devices.

Currently available septal closure devices present drawbacks, including technically complex implantation procedures. Additionally, there are significant complications due to thrombus, fractures of the components, conduction system disturbances, perforations of heart tissue, and residual leaks. Many devices have a high septal profile and include large masses of foreign material, which may lead to unfavorable body adaptation of a device. Given that ASD devices are designed to occlude holes, many lack anatomic conformability to the flap-like anatomy of PFOs. Thus, when inserting an ASD device to close a PFO, the narrow opening and the thin flap may form impediments to proper deployment. Even if an occlusive seal is formed, the device may be deployed in the heart on an angle, leaving some components insecurely seated against the septum and, thereby, risking thrombus formation due to hemodynamic disturbances. Finally, some septal closure devices are complex to manufacture, which may result in inconsistent product performance.

Various devices and delivery systems have been developed to deliver occluders and other medical devices through body lumens. Some delivery systems of the prior art are used to deliver devices that readily expand to a delivered configuration when removed from the delivery system. Other occluders do not readily expand into a deployed configuration and techniques are used to change the configuration of the device into the deployed configuration. In the latter case, once an occluder is delivered to the desired delivery site and deployed, the occluder must have a catch system that keeps the device in the deployed configuration.

The devices and techniques disclosed herein are designed to address these and other deficiencies of prior art septal closure devices and techniques for delivering and retrieving such devices.

SUMMARY OF THE INVENTION

Aspects of the invention include occluder devices and techniques for delivering an implant into a desired location within the body and securing the device in the deployed configuration. These delivery techniques relate particularly to, but are not limited to, septal occluders made from a polymer tube or substantially cylindrical body. These delivery techniques, in addition to use with septal occluders, could be applied to other medical devices, such as other expandable devices constructed from an underlying tubular structure. In one aspect, the present invention provides a catch system that holds the device in a deployed configuration when at the desired delivery site. In some embodiments, the catch system comprises a catch member that includes a flap that is configured to fit within the inner lumen of the proximal end of the occluder during delivery. When the flap is proximal to the end of the occluder, the catch system holds the device in the deployed configuration. According to some embodiments, the catch system maintains the shortened axial length of the device when the device has been deployed.

In some embodiments, the flap may have a rounded cross-section and the flap may comprise two or more wings which extend radially from the proximal end of the catch member. The flap can have a minimum thickness-to-width ratio of about 1 to about 2. Embodiments of the catch member with flap can be used advantageously with any of a number of securement systems to attach the device to the delivery system, including threaded systems and collet-type securement systems.

In one aspect, the invention provides a collapsible medical device for occluding an aperture in a body. The medical device has a first configuration with a reduced profile and a second configuration with an expanded profile and is adapted to be delivered through a delivery system into a desired delivery location. The device has a proximal side and a distal side, with an occluder portion movable between the first and second configurations, and a catch system for holding the medical device in the second configuration. The catch system includes a catch member with a flap at its proximal end that is bendable and the flap holds the medical device in the second configuration.

In some embodiments, the flap includes two wings. In some embodiments, the wings are separated by cutoff V-shaped notches. In some embodiments, the flap has a rounded surface at the radial outermost edge. In some embodiments, the flap has a rounded surface at the radially outermost surface. In some embodiments, the flap has an oval configuration. In some embodiments, the flap has a thickness to width ratio of about 1 to about 2. In some embodiments, the flap has two wings with rounded surfaces at the radially outermost surface. In some embodiments, the flap is disposed at the proximal most end of the catch member.

In some embodiments, a first force required to deform the flap for retrieval is greater than a second force required to deform the flap for deployment.

In some embodiments, the flap fits inside an interior passage of the occluder in during delivery and retrieval, and the flap has a first interference with the interior passage of the occluder during delivery and a second interference with the interior passage of the occluder during retrieval, and the second interference is greater than the first interference.

In some embodiments, the catch member has a first outer diameter distal from the flap and a second outer diameter proximal from the flap and the second outer diameter is greater than the first outer diameter.

In some embodiments, a base of the flap on the proximal side is curved and has a greater radius than a base of the flap on the distal side.

In another aspect, the invention provides a collapsible medical device for occluding an aperture in a body with a first configuration with a reduced profile and a second configuration with an expanded profile. The medical device is adapted to be delivered through a delivery system into a desired delivery location. The medical device includes an occluder portion that is adapted to move from a reduced profile configuration to an expanded profile configuration, with an axial passage along the length of the occluder. The medical device also includes a catch member adapted to be disposed in the passage such that the occluder can move from the reduced profile configuration to the expanded profile configuration with the catch member in the passage. The catch member includes a flap on the proximal end of the catch member that is able to move in an axial direction relative to a proximal end of the occluder portion. When the occluder is in the expanded profile configuration, the flap is disposed proximal to the axial passage such that it secures the occluder in the expanded profile configuration.

According to at least some embodiments, the device is formed from a tube. According to some embodiments, the tube includes a material selected from the group consisting of metals, shape memory materials, alloys, polymers, bioabsorbable polymers, and combinations thereof. In particular embodiments, the tube includes a shape memory polymer. In particular embodiments, the tube includes nitinol. In some embodiments, the tube is formed by rolling a flat piece of material into a tubular form. According to some embodiments, the device is formed by cutting the tube. In other embodiments, the device is formed from a plurality of filaments arranged in a tubular form. The device is placed in its deployment configuration by reducing the axial length of the device.

These and other aspects and embodiments of the disclosure are illustrated and described below.

BRIEF DESCRIPTION OF THE DRAWINGS

FIGS. 5-8 illustrate an occluder according to the present invention in a sequence between a reduced profile delivery configuration (FIG. 5) and an expanded profile deployed configuration (FIG. 8);

FIG. 15 is a cross-sectional side view of one step in a deployment sequence according to an aspect of the invention;

FIG. 16 is a transverse cross-section taken along lines 16-16 of FIG. 15;

FIG. 17 is a cross-sectional side view of an occluder with the catch system engaged;

FIG. 18A is a cross-sectional side view of the deployed occluder in process of retrieval;

FIG. 18B is a detail cross-sectional view of the flap and the interior wall of the occluder;

FIGS. 19-24 are cross-sectional side views of steps in a deployment sequence according to an aspect of the invention;

DETAILED DESCRIPTION OF THE ILLUSTRATED EMBODIMENTS

Figure 1:
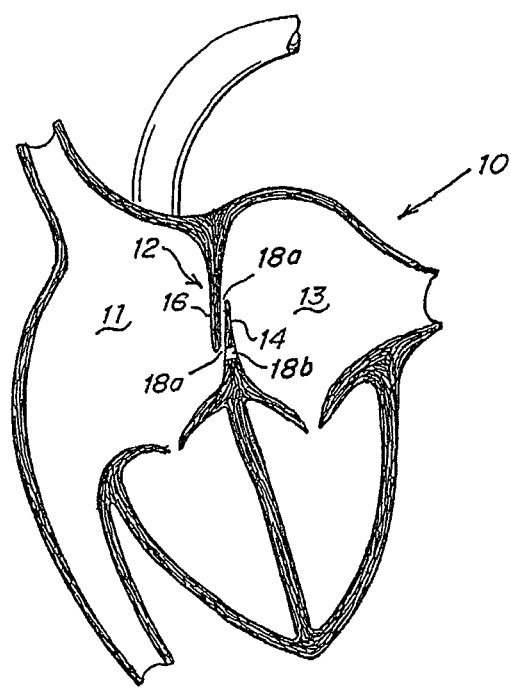
FIG. 1 is a schematic representation of a human heart including various septal defects.

Aspects of the present invention include devices, delivery/retrieval systems and techniques for delivering such devices intended to occlude an aperture within body tissue. In particular and as described in detail below, the described occluder may be used for closing an ASD, VSD (ventricular septal defect) or PFO in the atrial septum of a heart. Although the embodiments are described with reference to an ASD, VSD or PFO, one skilled in the art will recognize that the device and methods of the present invention may be used to treat other anatomical conditions. As such, the invention should not be considered limited in applicability to any particular anatomical condition. In addition, the systems and methods for delivery and retrieval, and for catching a device in a deployed state, which are aspects of the present invention may also be used in connection with other types of devices besides an occluder, in particular, devices having tubular profiles.

In this application, "distal" refers to the direction away from a catheter insertion location and "proximal" refers to the direction nearer the insertion location. Additionally, the term "delivery configuration" refers to the configuration of a device, such as an occluder, when it has a reduced profile in a delivery catheter. The term "deployed configuration" refers to the configuration of the device, such as an occluder, when it has deployed from the catheter, such as at the desired implantation location. The reference numerals used to identify components of the described embodiment are disposed on multiple figures where the component is illustrated. The reference numerals are intended to facilitate an overall understanding of the invention and the relationship between components illustrated in different figures.

In this application, "resilient" refers to a property of a material to deform (e.g., to change shape) elastically when a deforming force is applied, and then, upon cessation of the deforming force, recover its pre-deformation shape.

FIG. 1 illustrates a human heart 10, having a right atrium 11 and a left atrium 13 and including various anatomical apertures 18a and 18b. The atrial septum 12 includes septum primum 14 and septum secundum 16. The anatomy of the septum 12 varies widely within the population. In some people, septum primum 14 extends to and overlaps with septum secundum 16. The septum primum 14 may be quite thin. When the anatomical apertures 18a is present, blood could travel through the anatomical aperture 18a between septum primum 14 and septum secundum 16, referred to as "the PFO tunnel". Additionally or alternatively, blood could travel through anatomical aperture 18b, referred to as an ASD.

Figure 2:
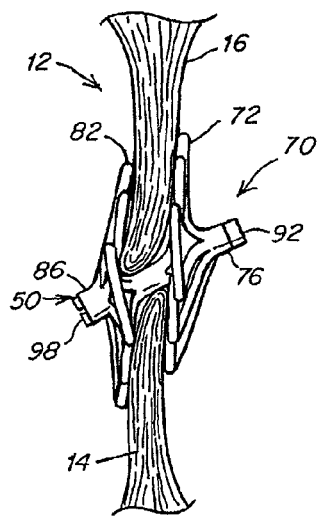
FIG. 2 illustrates a deployed occluder according to an aspect of the disclosure.

FIG. 2 illustrates an exemplary occluder with which systems and techniques disclosed herein may be used. An occluder 70, for example, is illustrated as deployed in the septum 12 of a heart. The device operates to close an aperture in the septum by covering both sides of the aperture. The occluder 70 in FIG. 2 is shown in a human heart in a deployed configuration with a catch member 50 engaged (much of the catch member is obscured by the central tube of the occluder).

Figure 3:
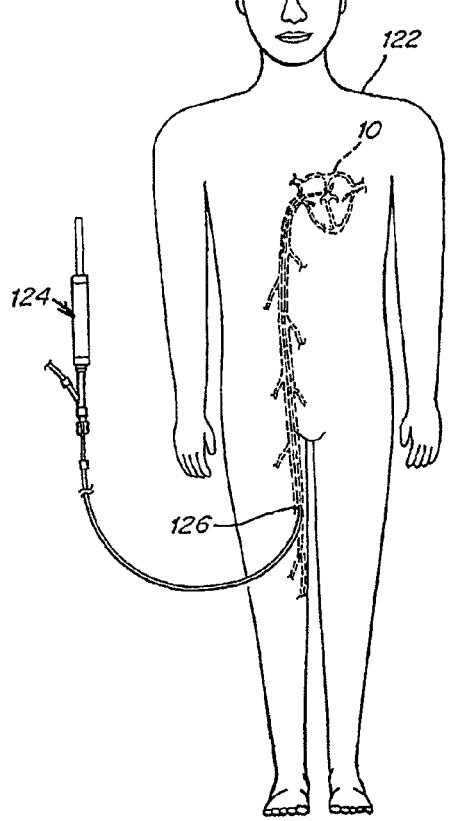
FIG. 3 illustrates introduction of the occluder in a human heart using a delivery system in accordance with an aspect of the disclosure.
Figure 4:
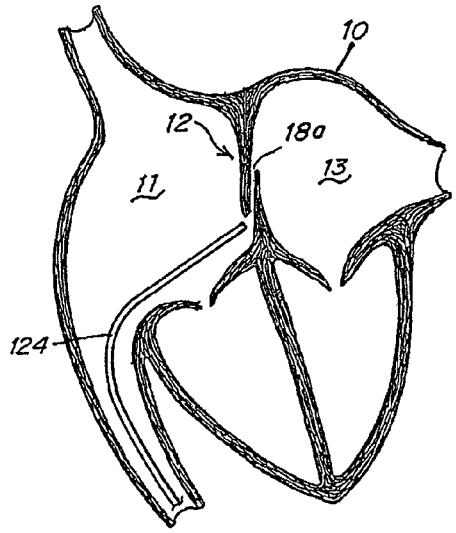
FIG. 4 illustrates a detail view of a delivery catheter in a heart with its tip approaching a patent foramen ovale between the left atrium and right atrium.

FIG. 3 illustrates the insertion of an occluder in a human subject 122 using a delivery assembly 124 in accordance with an aspect of the disclosure. A portion of delivery assembly 124, including an occluder and a delivery mechanism for the occluder, which can be externally manipulated by a clinician, is inserted into the subject through an incision point 126. The distal end of the delivery assembly is advanced toward and into the heart 10 until the distal end is in proximity to the defect to be closed, as seen in FIG. 4.

The embodiment described in conjunction with FIGS. 5-8 has some similarities to the devices disclosed in and/or can be used with catch systems and delivery systems and techniques described in U.S. patent application Ser. No. 10/890,784, entitled Tubular Patent Foramen Ovale (PFO) Closure Device with Catch System, filed on Jul. 14, 2004; U.S. patent application Ser. No. 11/384,635, filed Mar. 20, 2006, entitled Catch Member for PFO Occluder; U.S. patent application Ser. No. 11/235,661, filed Sep. 26, 2005, entitled Occluder Device Double Securement System for Delivery/Recovery of Such Occluder Device; U.S. patent application Ser. No. 11/395,718, entitled Tubular Patent Foramen Ovale (PFO) Closure Device with Catch System, filed Mar. 31, 2006; U.S. Prov. Patent Application No. 60/847,703, entitled Implant-Catheter Attachment Mechanism Using Snare and Method of Use, filed Sep. 28, 2006; U.S. patent application Ser. No. 11/644,373, entitled Catch Members for Occluder Devices, filed Dec. 21, 2006; U.S. patent application Ser. No. 11/729,045, entitled Screw Catch Mechanism for PFO Occluder and Method of Use, filed Mar. 28, 2007; U.S. patent application Ser. No. 11/728,694', entitled Patent Foramen Ovale (PFO) Occlusion Device with Linearly Elongating Petals, filed Mar. 27, 2007; U.S. patent application Ser. No. 11/121,833, entitled Catching Mechanism for Tubular Septal Occluder, filed May 4, 2005; all of which have the same assignee as the present application, and are incorporated herein by reference in their entirety.

As shown in FIGS. 5-8, the occluder 70 is formed from a tube (which can be extruded or rolled) that forms distal petals 72 produced by slits 74 in the distal portion of tube according to the cutting pattern shown in FIG. 5. As shown in FIG. 6, the distal portion 20 of the tube includes eight slits 74 that form eight extended segments of the tube that form the distal loops or petals 72. As apparent from the figures, the slits extend the entire distance of the distal portion of the tube between central tube 78 and distal end 76 so that the loops of the same cross-section are formed. Upon application of force $F_d$ to distal end 76, extended segments defined by slits 74 bow and twist outward to form distal petals 72 in distal side of the occluder 70. The movement of the segments during deployment is such that the segments rotate in an orthogonal plane relative to the axis of the device. Central tube 78 may be constrained during the application of force $F_d$, or any combination of forces sufficient to reduce the axial length of the tube may be applied. One end of each of distal petals 72 originates from central tube 78, while the other end originates from distal end 76 (FIGS. 6 and 7). Proximal petals 82 may be formed in proximal portion 40, as shown in FIGS. 6-8, making slits 84 between central tube 78 and proximal end 86, using the same cutting pattern described above and applying force $F_p$ or combination of forces sufficient to reduce the axial length of the tube allowing slits 84 to bow and twist outward to form proximal petals 82 in proximal portion 40 of the occluder 70. One end of each of distal petals 82 originates from central tube 78, while the other end originates from proximal end 86. In alternate embodiments, occluder 70 could be formed of filaments disposed radially equidistant around a longitudinal axis to define a tubular shape and then bonded at selected locations to provide joints at the end and in the center.

The tube(s) or filaments forming occluder 70 may be formed from a biocompatible metal or polymer. In at least some embodiments, the occluder 70 is formed of a bioabsorbable polymer, or a shape memory polymer. Shape memory polymers can be advantageous so that the structure of the device assists in pressing the PFO tunnel closed. In other embodiments, the occluder 70 is formed of a biocompatible metal, such as a shape memory alloy (e.g., nitinol). The thermal shape memory and/or superelastic properties of shape memory polymers and alloys permit the occluder 70 to resume and maintain its intended shape in vivo despite being distorted during the delivery process. Alternatively, or additionally, the occluder 70 may be formed of a bioabsorbable metal, such as iron, magnesium, or combinations of these and similar materials. Exemplary bioabsorbable polymers include polyhydroxyalkanoate compositions, for example poly-4-hydroxybutyrate (P4HB) compositions, disclosed in U.S. Pat. No. 6,610,764, entitled Polyhydroxyalkanoate Compositions Having Controlled Degradation Rate and U.S. Pat. No. 6,548,569, entitled Medical Devices and Applications of Polyhydroxyalkanoate Polymers, both of which are incorporated herein by reference in their entirety.

The cross-sectional shape of the tube may be circular or polygonal, for example, square or hexagonal. The slits 74 and 84 may be disposed on the face of the polygon (i.e., the flat part) or on the intersection of the faces.

The tube can be injection molded, extruded, or constructed of a sheet of material and rolled into a tube. The sheet of material could be a single ply sheet or multiple ply. The slits that form the segments could be cut or stamped into the sheet prior to rolling the sheet into a tube to connect the ends to form an enclosed cross-section. Various geometrical cross-sections are possible including circular, square, hexagonal and octagonal and the joint could be at the vertex or along the flat of a wall if the cross-section is of a particular geometry. Various attachment techniques could be used to join the ends of the sheet to form a tube, including welding, heat adhesives, non-heat adhesives and other joining techniques suitable for in-vivo application.

The transformable design of occluder 70 enables occluder 70 to be delivered in a low profile, delivery configuration and to be converted readily, i.e., by reducing the axial length, in place to the high profile deployed configuration. Moreover, the conversion can readily be effected by forcing distal end 76 and proximal end 86 together. For example, distal portion 20 and proximal portion 40 of occluder 70 may be deployed in separate steps, or both distal portion 20 and proximal portion 40 of occluder 70 may be exposed (e.g., out of the delivery catheter) prior to engaging the catch system and deployed together as the catch element is engaged. Use of the terms distal and proximal portion 20 and 40, respectively, include the loops or other geometries and configurations that are formed on the distal and proximal sides, respectively.

Occluder 70 may be made in any one of several ways. Slits 74 and 84 may be cut such that tube bends into its intended configuration following deployment in vivo. Specifically, slits 74 and 84 may be cut to produce segments 72 and 82 (as illustrated in FIGS. 5, 6) of a thickness that facilitates the bending and formation of loops 72 and 82 (as illustrated in FIGS. 7, 8) upon the application of forces $F_d$ and/or $F_p$ during deployment. The segments 72 and 82 that form the loops are referenced with the same reference numeral. As an alternative, or additionally, a tube formed of a shape memory material may be preformed into its intended configuration ex vivo so that it will recover its preformed shape once deployed in vivo. According to at least some embodiments, this preforming technique produces more reliable deployment and bending of occluder 70 in vivo. An intermediate approach may also be used: tube may be only slightly preformed ex vivo such that it is predisposed to bend into its intended shape in vivo upon application of forces $F_d$ and/or $F_p$. These techniques could also be used when the device is formed by bonding filaments together.

This particular type of occluder 70 and delivery sequences are described for purposes of illustration and explanation; of course, other types of occluders can be deployed using the deployment catch systems described herein. The petal configuration, illustrated in FIG. 8, is the deployed configuration. The occluder 70 can be secured in the petal configuration by a catch system that holds the ends of the tube together, certain embodiments of which are described below.

In general, references to "occluder 70" herein may be inclusive of catch member 50 (or 50a), depending on the context, for example, unless separately listed or otherwise stated. The catch member 50, as illustrated, is disposed in an axial passage, in a radially central location, in the occluder 70 and is schematically illustrated as a separate piece than the occluder 70. In a preferred embodiment, the catch member may be fixed to one end of the tube that forms occluder 70. For example, a flange 92 provided at the distal end of the catch member may be fixed to the distal end of the occluder 70. One end of the tube, preferably the proximal end of the tube, is able to move with respect to the catch member 50 (or 50a) (and especially the catch system) so that the distal and proximal petals 72 and 82 can move from the delivery configuration to the deployed configuration. The inside surface of the tube is able to slide over the catch member 50 (or 50a) and particularly the proximal end, until the proximal end 86 of the occluder 70 rests against a distal surface of the proximal flap of the catch member 50 or 50a, such that the occluder 70 is secured in its deployed configuration. The catch member 50 (or 50a) cooperates with a delivery system and includes a portion for connection to the delivery/recovery system, including, for example, a threaded section illustrated and described in more detail below.

Figure 9:
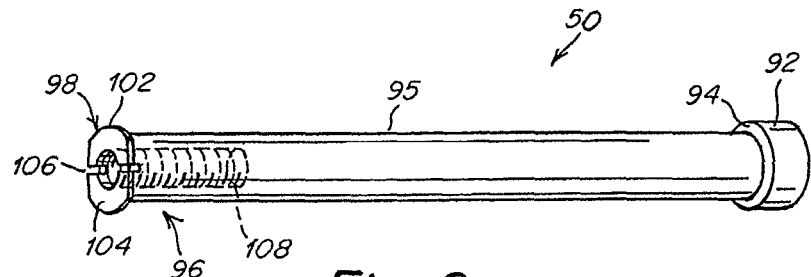
FIG. 9 is a detail view of a catch member in accordance with an embodiment of the present invention.

The catch system will now be described with reference to FIGS. 9-18B. FIG. 9 illustrates the catch member 50 that can be disposed in the axial passage of the occluder 70. The catch member 50 includes a distal flange 92 that is disposed at the distal end of the occluder 70. In some embodiments, the distal flange 92 of the catch member is fixed to the occluder 70. In other embodiments, the catch member 50 is allowed to rotate with respect to the occluder 70. In one embodiment, the catch member 50 includes a distal shelf 94 that allows the distal end of the occluder 70 to move proximally when applying force $F_d$ (see, for example, FIG. 6). Typically, the catch member 50 has an axial length of about 5-30 mm and a diameter of approximately 0.5-3 mm. Although a circular cylinder is illustrated, a variety of cross-sectional shapes can by used effectively.

Figure 10:
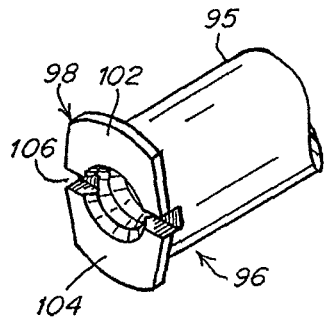
FIGS. 10-12 are detail views of the proximal end of the catch member according to various embodiments of the present invention.
Figure 11:
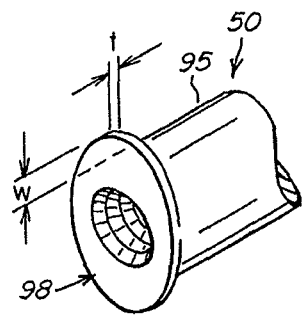

The catch member 50 includes a catch body 95 and a proximal side 96 with a flap 98, which provides the catch surface. The catch body 95 has a cylindrical or tubular shape. In some embodiments, the catch body 95 substantially spans the length of the occluder 70 in the deployed configuration. The flap 98 protrudes radially from the catch body 95, as illustrated in FIG. 11. The operation of the catch system using a flap-type catch mechanism is described in detail below. It is understood that a flap (e.g., flap 98), as used herein, can include multiple wings (e.g., 2, 3, 4, 5, 6, or more wings). Wings may or may not be separated by one or more slots. A flap can also provide uninterrupted circumferential coverage around the catch member, e.g., as illustrated in FIG. 11. With continued reference to FIG. 9, the flap 98 includes two wings 102, 104, and a planar slot 106 running transverse through the axis of the catch member 50. Wings 102 and 104 are separated by slot 106, leaving a portion of the proximal side without wings. The purpose of slot 106 is described below. According to some embodiments of the invention, wings 102 and 104 are slightly squared off such as illustrated FIG. 10. According to other embodiments of the invention, wings 102 and 104 have rounded edges as illustrated in FIG. 10. FIG. 9 also illustrates (in phantom lines) internal threads 108 that are used to secure the catch member 50 to the delivery system. FIG. 10 is an enlarged perspective view of the proximal side 96 of the catch member 50 of FIG. 9.

FIG. 11 illustrates an alternate embodiment of the catch member 50 with the flap 98 according to an aspect of the present invention. Specifically, the proximal side 96 of the catch member 50 includes a flap 98 formed in an oval shape as viewed from the proximal end of the catch member. While certain configurations are illustrated herein, the flap 98 and wings 102 and 104 can have any suitable shape, such as rounded, square, or polygonal. The flap 98 and various configurations thereof can provide advantages as described below.

In some embodiments, the flap has a thickness (t) to width (w) ratio of at least about 1 to about 2. As illustrated in FIG. 11, the width is the radial distance the flap extends beyond the diameter of the catch body 95 of the catch member 50; the thickness is the extension of the flap in the axial direction of the catch member 50. In a preferred form, the thickness may be about 0.005 inch and the width may be about 0.010 inch. In some embodiments, flap 98 is formed of a resilient material that allows the flap to deform, such as to change shape by bending, and then recover. The deformable flap 98 provides a greater diameter at the proximal end of the catch member 50, relative to the body 95 of the catch member 50, and relative to a proximal end of the occluder axial passage.

Figure 12:
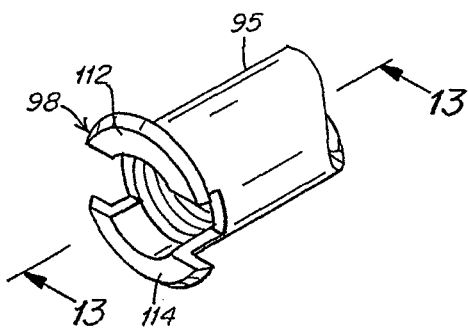
Figure 13:
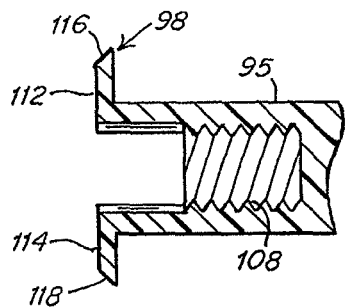
FIG. 13 is a cross-sectional view taken along lines 13-13 of FIG. 12.

FIGS. 12 and 13 illustrate another embodiment of the catch member 50 where wings 112 and 114 have an angled outer edge. According to other embodiments of the invention, the flap can also extend the entire circumference around the catch member 50. FIG. 12 is a detail perspective view of the proximal side of a catch member 50 and FIG. 13 is a cross-sectional view taken along lines 13-13 in FIG. 12. As illustrated, wings 112 and 114 include angled radially outward facing edges 116 and 118. The angled edges 116 and 118 can help control the catch mechanism of the invention together with the width and thickness of the particular flap. The edges 116 and 118 could also be squared off, or rounded or have any other suitable shape.

Figure 30A:
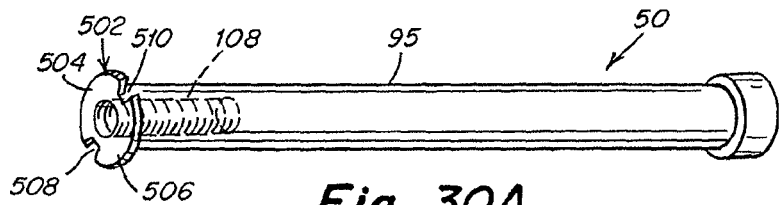
FIG. 30A is a perspective side view of an alternate embodiment of a catch member according to an aspect of the invention.
Figure 30B:
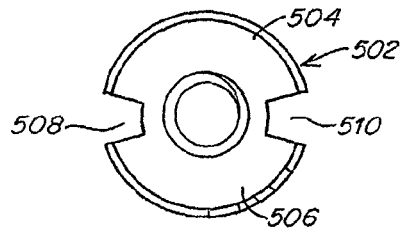
FIG. 30B is an end view of an alternate embodiment of a catch member according to an aspect of the invention.

FIGS. 30A and 30B illustrate a perspective side view and an end view of the proximal end of an alternative embodiment of catch member 50, including a flap 502 having a first segment 506 and a second segment 504. The segments 506 and 504 are portions of an annulus, separated by squared off V-shaped notches 508 and 510. The notches 508 and 510 could also have other shapes suitable for a given application.

Figure 14:
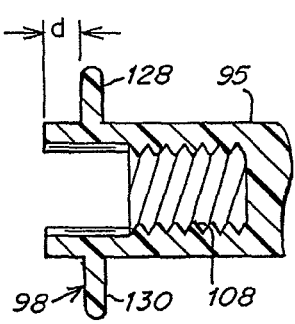
FIG. 14 is a cross-sectional side view of the catch member according to another embodiment of the present invention with rounded edges on a flap.

FIG. 14 illustrates a prospective cross-section view taken along the catch member 50 and illustrates a flap with rounded cross-sections 128 and 130, according to one embodiment of the invention. Additionally, according to one embodiment of the invention, the flap can be situated at the proximal tip of the catch member as illustrated in FIGS. 10-13, or set back from the proximal tip of the catch member by a distance d as illustrated in FIG. 14.

The embodiments described herein allow for a larger outer diameter of the proximal end of the catch member 50, relative to a dimension of the occluder 70, such as the inner diameter of the passage of the occluder 70 at the proximal end, or in other embodiments, the outer diameter of the proximal end of the occluder 70, to securely catch the occluder 70 in its deployed configuration. The embodiments described herein also at the same time allow deployment of the occluder 70 to occur readily by application of an appropriate amount of force, which causes the proximal end of the occluder 70 to slide distally over the flap 98. Alternative embodiments in which the securement force may be increased relative to the deployment force are discussed further herein below.

The flaps 98 described herein provide a balance between ease of deployment of an occluder and security of the catch in the deployed configuration of the catch member and the deployed configuration of the occluder 70 that has not been achieved by designs hitherto available.

Additionally, the flaps 98 provides a smaller profile in the right atrium due to its relative thinness. The smaller flap profile reduces the possibility of thrombus formation due to blood flow disruptions in the right atrium.

The operation of the catch system during the delivery of an occluder 70 is described in connection with FIGS. 15-18B. FIG. 15 illustrates a partial detail view of the delivery of an occluder 70 with the flap catch system. The catch member 50 is attached to an inner delivery wire 346 by a threaded connection 58. As illustrated, male threads on the distal end of delivery wire 346 are threaded into female threads on the proximal end of the catch member 50. The female threads could also be disposed at other locations along the length of the occluder 70. Of course, it will be understood that in any threaded connection described herein, reversal of male and female threads is also possible. As illustrated in FIG. 15, the occluder 70 is attached to a delivery catheter 356 by a threaded connection. As illustrated, the proximal end 86 of the occluder includes male threads and the delivery catheter 356 includes female threads. The delivery wire 346 and delivery catheter 356 can be manipulated such that the position of the proximal end 96 of the catch member 50 can be moved with respect to the proximal end 86 of the occluder 70. During the deployment of occluder 70, the proximal end 96 of the catch member 50 is pulled toward the proximal end 86 of the occluder 70. The inner diameter of the proximal end 86 of the occluder 70 is sized to be slightly larger than the outer diameter of the catch body 95 of the catch member 50, but not larger than the combined diameter of the catch body 95 and the width of the flap 98 (or the overall outer diameter of the proximal end of the catch member 50). The sizing of the inner diameter of the occluder 70 relative to the overall outer diameter of the proximal end 96 of the catch member 50 forces the flap 98 to bend distally when the occluder 70 is being forced over the flap 98 into the secure deployed configuration, as illustrated in FIG. 15.

In a particularly preferred embodiment, the overall outer diameter of the proximal end of the catch member 50 including the flap 98 is about 0.090 inch and the inner diameter of the proximal end of the occluder 70 is about 0.070 inch. The occluder can be made of a material that allows for some radial and/or axial deformation (for example, expansion), when the flap 98 is being moved through (as illustrated in FIG. 15). Alternatively, the occluder 70 can be made of a material that does not provide any radial and axial resilience when the flap 98 is moved through. FIG. 16 is an axial view of the flap 98 being deformed as it moves through the occluder.

FIG. 17 illustrates the configurations of occluder 70 and catch member 50 after the catch member 50 has been moved entirely through the occluder 70 and the flap is on the proximal side of the occluder 70. The catch member 50 has engaged and holds the occluder in the deployed configuration. In this configuration, where the relative position of the flap 98 and the occluder 70 are as illustrated, the delivery wire 346 and catheter 356 still hold the position of the catch member and the occluder, respectively, which allow for visualization (by fluoroscopy, for example) of the position of the occluder 70 and to confirm if placement of the occluder 70 is as desired. In one embodiment, as illustrated in FIG. 17, the overall outer diameter of the proximal end of the catch member 50 including the flap 98 is smaller than the distal portion of the delivery catheter 356. In one embodiment, as illustrated in FIG. 17, the flap 98 can be so dimensioned that the flap 98 rests on the proximal surface of the proximal end 86 of the occluder 70 when the occluder 70 is in a fully deployed position with the catch system engaged. In the disclosed embodiment, the flap 98 has enough radial strength to hold the occluder 70 in the deployed condition without deformation.

FIGS. 18A and 18B illustrate configurations of the occluder 70 and the catch member 50 during retrieval of the occluder 70, as the catch member 50 is moving back into the axial passage of the occluder 70. FIG. 18B is a detail view of the flap 98 moved into the axial passage of the proximal end of the occluder 70. In the disclosed embodiment, the flap 98 has sufficient flexibility to be pushed back into the axial passage of the occluder (or the axial passage of the occluder to be pulled over the flap) so that the retrieval of the device can occur. In accordance with certain embodiments of the invention, as illustrated in FIG. 18B, the flap 98 is bent proximally for retrieval. In accordance with other embodiments of the invention, as illustrated in FIG. 15, the flap 98 is bent distally for delivery.

Deployment of the occluder to a desired site is typically a multi-step operation. In FIGS. 5-8, the occluder 70 is shown outside the delivery catheter for purposes of illustration. As shown in FIG. 19, the delivery sheath 342 contains both the occluder 70 in its reduced profile, delivery configuration, and a disengaged catch member 50. As discussed above with reference to FIGS. 3 and 4, the distal end of the delivery sheath 342 (part of delivery assembly 124 illustrated in FIGS. 3 and 4) with the enclosed occluder 70, is first inserted into the right atrium 11 of the patient's heart. The distal end of the delivery sheath 342 with the enclosed occluder 70 is next inserted through the anatomical aperture 18a, located in the septal tissue 12, into the left atrium 13. The distal portion 20 of occluder 70 is then deployed into the left atrium 13. The deployment process is described further below.

Figure 21:
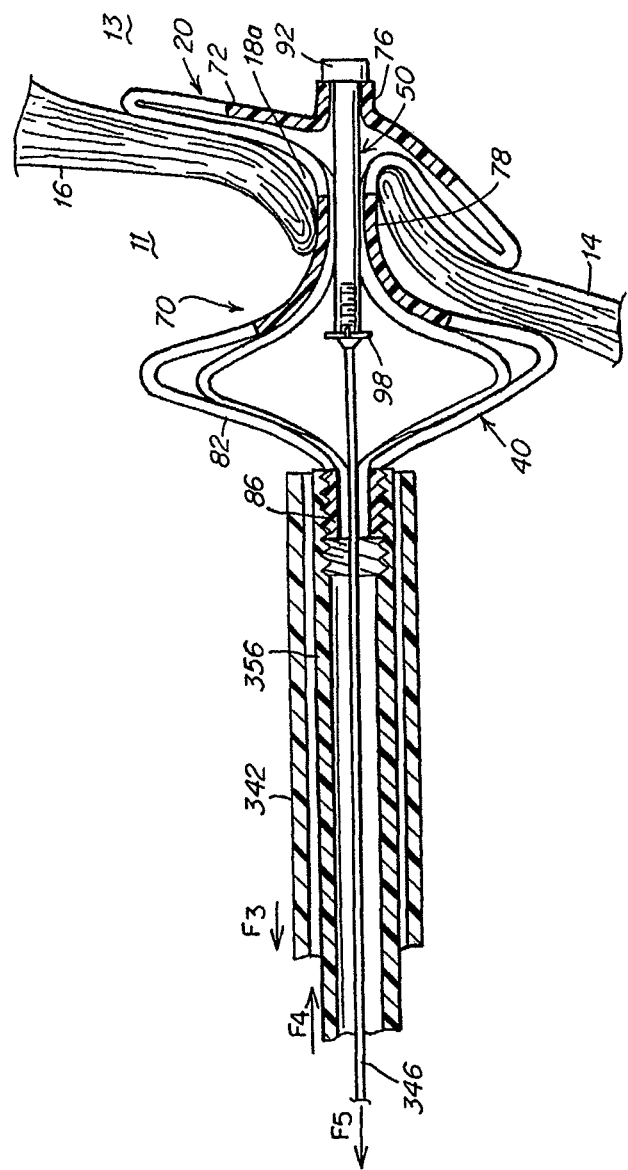
Figure 22:
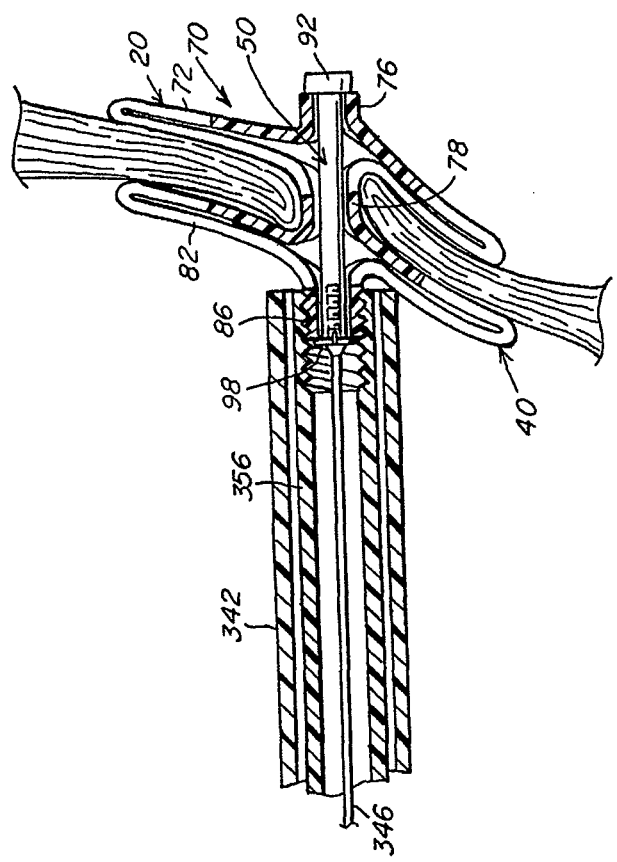
Figure 23:
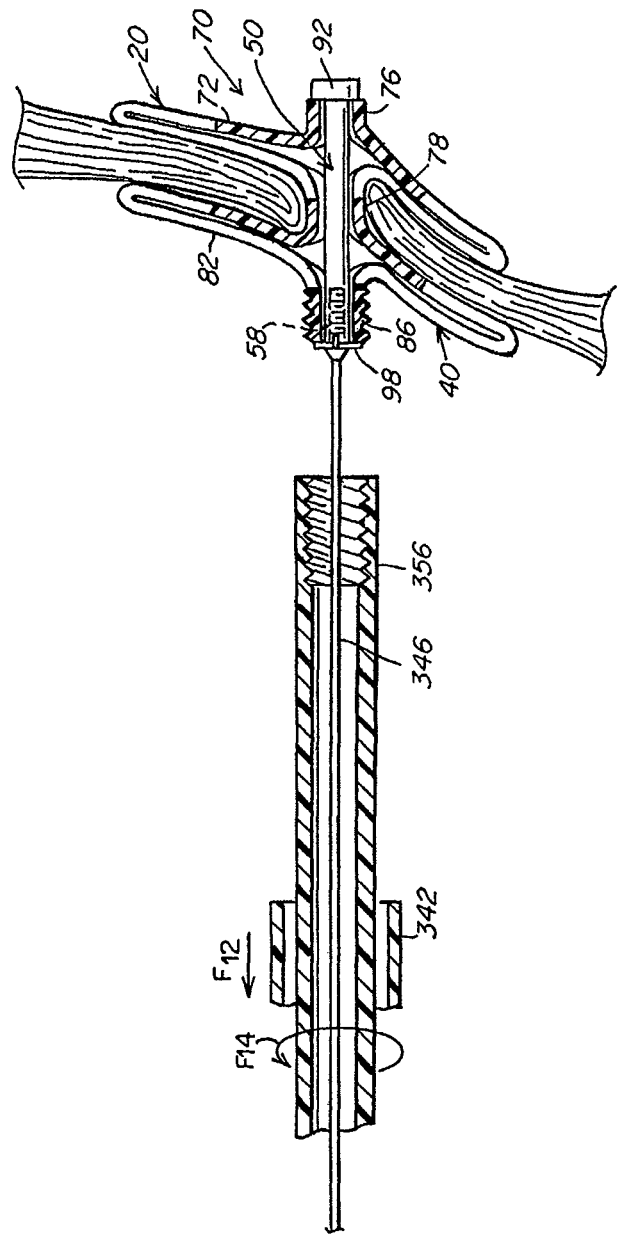
Figure 24:
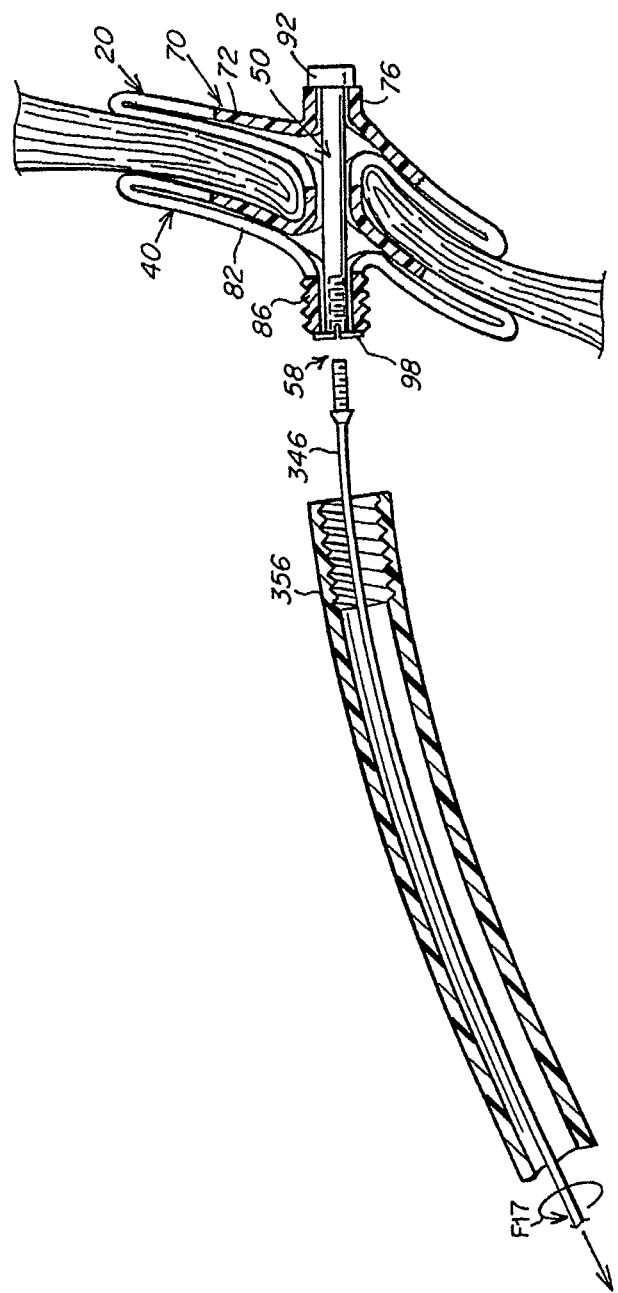

As shown in FIG. 20, the distal portion 20 of the occluder is deployed in the left atrium 13, so that the central tube 78 of the occluder 70 is positioned at the anatomical aperture 18a. As shown in FIG. 21, the proximal portion 40 of the occluder 70 is then deployed into the right atrium 11. Upon proper deployment, the central tube 78 is typically disposed at the anatomical aperture 18a, and the distal portion 20 and proximal portion 40 exert a compressive force against septum primum 14 in the left atrium 13 and septum secundum 16 in the right atrium 11, respectively, to close the anatomical aperture 18a (e.g. a PFO), as illustrated in FIG. 22. As illustrated in FIGS. 23-24, when the occluder 70 is properly deployed, the delivery system is detached from the occluder 70, and the delivery sheath 342 with the delivery catheter 356 and delivery wire 346 are then withdrawn from the heart. In the event that the occluder 70 is not properly deployed after performing the procedure described above, the occluder 70 can be recovered by reversing the steps of the delivery sequence.

Referring again to FIG. 19, the catch member 50 and the occluder 70 are secured to the delivery wire 346 and to the delivery catheter 356, respectively. The female threaded portion of the delivery catheter 356 is screwed onto the male threaded portion of the occluder 70. The male threaded portion of the delivery wire 346 is screwed onto the female threaded portion of the catch member 50.

Referring now to FIG. 20, the distal portion 20 of the occluder 70 is deployed on the distal side of the aperture in the left atrium 13. The distal portion 20 is deployed by first retracting the delivery sheath 342 to expose the distal portion 20 of the occluder 70. The axial length of the occluder 70 is then reduced by applying pulling force $F_1$ on delivery wire 346 with sufficient force to cause the proximal end of the catch member (with the flap 98) to be pulled through the central tube 78 of the occluder 70 and the distal portion 20 of the occluder 70 to compress and distal petals 72 to form. Force $F_2$ is simultaneously applied to the delivery catheter 356 to hold the occluder 70 stationary. The central tube 78 of the occluder 70 catches on the flap 98 of the catch member 50, creating a temporary catch. This temporary catch holds the distal petals 72 in place while the remainder of the deployment sequence is carried out.

Referring now to FIG. 21, the proximal portion 40 of the occluder 70 is deployed on the proximal side of the aperture in the right atrium 11. This deployment is effected by first retracting the delivery sheath 342 to expose the proximal portion 40 of the occluder 70. The proximal petals 82 are then deployed by simultaneously advancing the delivery catheter 356 by applying force $F_4$ and retracting the delivery wire 346 by applying force $F_5$ to maintain the position of the occluder 70. Eventually, the proximal end of the catch member 50 is pulled through the axial passage of the proximal end of the occluder 70. The flap 98 reversibly deforms as illustrated in FIGS. 15 and 16. Specifically, the flap 98 on the catch member 50 bends away from the direction of travel. When the flap 98 is moved beyond the proximal end of the occluder 70, the deforming force no longer applies to the flap 98, allowing the flap 98 to bend toward into an upright configuration as illustrated in FIG. 17. The final configuration is illustrated in FIG. 22 and the flap is in the position illustrated in FIG. 17. The occluder 70 can now be evaluated for proper deployment at the desired location.

The occluder 70 can be evaluated for proper deployment with the delivery system attached or at least partially detached. The delivery system can be partially detached by releasing the delivery catheter 356 from the occluder 70 or by releasing the delivery wire 346 from the catch member 50. As shown in FIG. 23, according to one preferred embodiment, to evaluate the proper deployment of the occluder 70, if desired, the delivery sheath 342 can be further retracted and the delivery catheter 356 can be detached from the occluder 70. The delivery catheter 356 can be detached by applying torque to unscrew it from the proximal threaded portion of the occluder 70, and withdrawing the delivery catheter proximally. The delivery wire 346 continues to secure the catch member 50, and the occluder 70 through the catch system, as illustrated in FIG. 23. This affords the clinician a substantially unobstructed view of the occluder delivery site in order to evaluate the placement of the occluder 70. In addition, the more flexible distal portions of the delivery wire 346 and the delivery wire 346 allow the distal end of the delivery system and the deployed occluder 70 to be re-positioned so that the view is not obstructed. The positioning of the occluder 70 can be evaluated using fluoroscopy or other appropriate techniques. If the delivery or deployment of the occluder 70 is not satisfactory, then the delivery system can be used to retrieve the occluder 70. If delivery catheter 356 has been detached, it can be reattached by advancing the delivery catheter 356 proximally toward the threaded proximal portion of the occluder 70 and applying torque until the delivery catheter 356 is threaded onto the occluder 70. According to an alternative embodiment of the invention, delivery catheter 356 remains attached to the occluder, while the delivery wire 346 is detached and retracted during evaluation of the deployment.

Once the occluder 70 is successfully deployed, the delivery system can be detached in the sequence shown in FIGS. 23-24. As illustrated in FIG. 23, the delivery sheath 342 is retracted proximally by applying force $F_{12}$. The delivery catheter 356 is detached by applying torque $F_{14}$ to unscrew the threaded portion of the delivery catheter 356 from the threaded portion of the occluder 70. Delivery catheter 356 is then retracted proximally. The occluder 70 remains attached to the delivery system by the securement system provided by the delivery wire 346 and the catch member 50. As discussed above, if retrieval is desired for any reason, the occluder 70 can readily be returned to its low-profile configuration and removed at this point. As shown in FIG. 23, the delivery catheter 356 can be further retracted proximally to provide an unobstructed view of occluder 70, again while the delivery wire 346 remains attached to the catch member 50. As illustrated in FIG. 24, if the deployment is successful, then the delivery wire 346 can be detached by applying torque $F_{17}$ to unscrew the threaded portion of the delivery wire 346 from the threaded portion of the catch member 50. The torque applied to remove the delivery wire 346 and the delivery catheter 356 can independently be either clockwise or counterclockwise, depending on the design. Once detached from the catch member 50, the delivery wire 346 can be retracted proximally. The occluder 70 is now fully deployed. According to an alternative embodiment, delivery catheter 356 remains attached to the occluder during evaluation, while delivery sheath and delivery wire 346 are detached and retracted proximally. During final release, delivery catheter 356 is detached lastly.

If the design of the occluder 70 is such that the catch member 50 is allowed to rotate with respect to the occluder 70, i.e. when the distal end of the catch member 50 (for example, distal flange 92) is not fixed to the distal end of the occluder 70, a slot 106 on the proximal end of the catch member (shown in FIGS. 15, 17, and 18A) and a blade (not shown) that cooperates with the slot 106 on the delivery wire 346, may be used to prevent the catch member 50 from rotating during deployment. According to one embodiment of the invention, the slot 106 can be of many different shapes and sizes.

Figure 25:
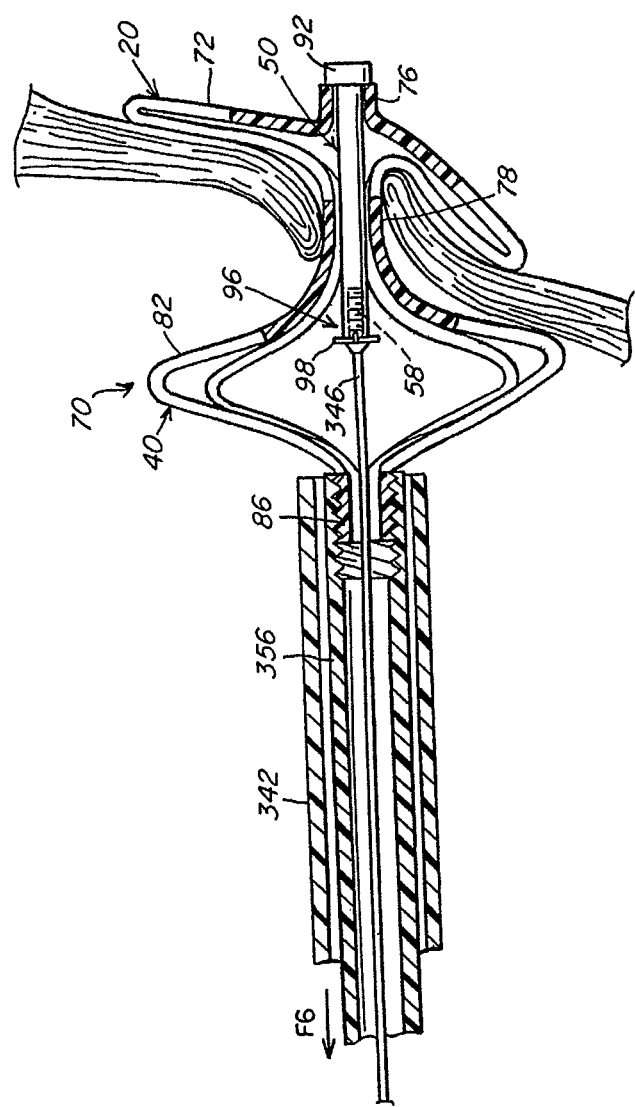
FIGS. 25-28 are cross-sectional side views of steps in a retrieval sequence according to an aspect of the invention.
Figure 26:
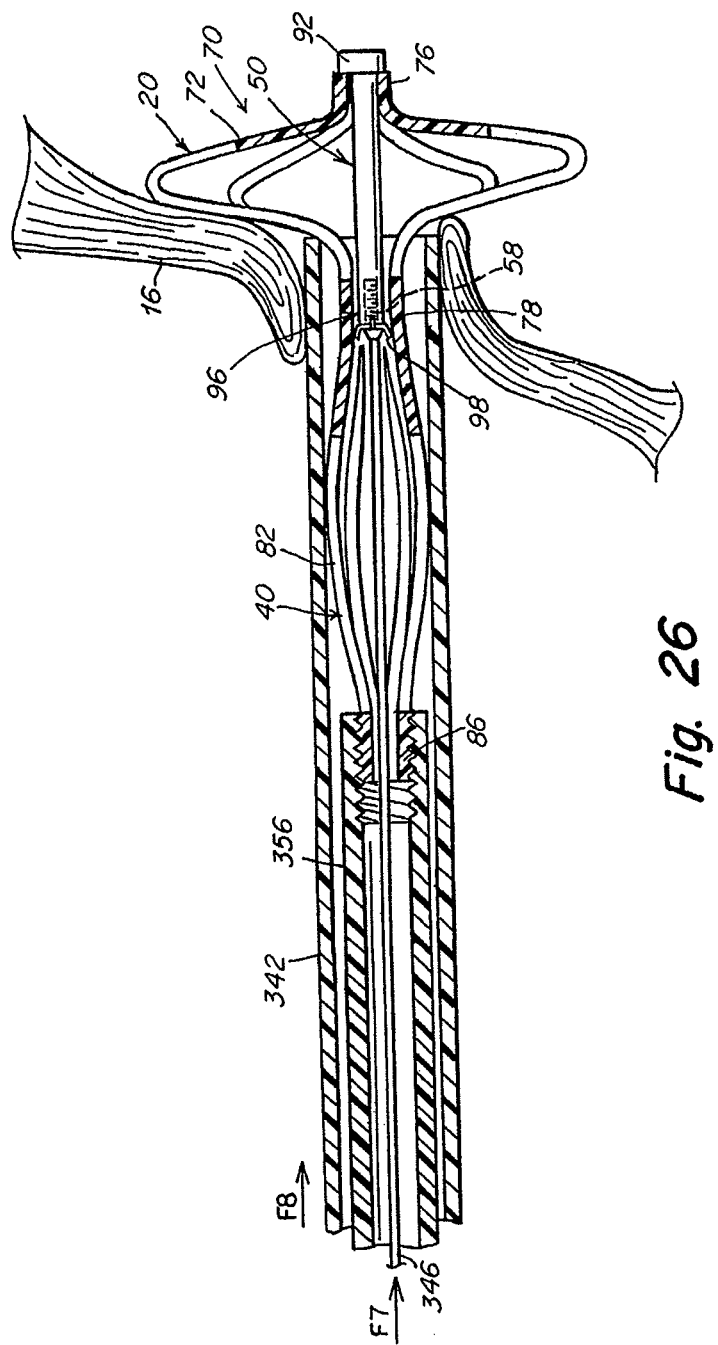

Referring now to FIG. 25, if retrieval is desired while the delivery wire 346 is still attached to the catch member 50, the process involves reattaching the delivery catheter 356 as mentioned above. Then force $F_6$ is applied to the delivery catheter 356 to pull the proximal portion 40 of the occluder 70 over the proximal end 96 of the catch member 50 so that the flap 98 is forced through the axial passage of the proximal end of the occluder 70. As the axial length of the occluder 70 is increased, the proximal petals 82 are unformed and the proximal portion 40 of the occluder 70 returns to its tubular profile. Referring to FIG. 26, force $F_8$ is applied to the delivery sheath 342 to advance the delivery sheath over the proximal portion 40 of the occlude 70 and retain the proximal portion 40 of the occluder 70 in the low-profile configuration. Also, force $F_7$ is applied to delivery wire 346 in order to collapse the distal portion 20 of the occluder 70 and further increase the axial length of the occluder 70. Alternatively, the same result can be achieved pushing distally on delivery catheter 356.

Figure 27:
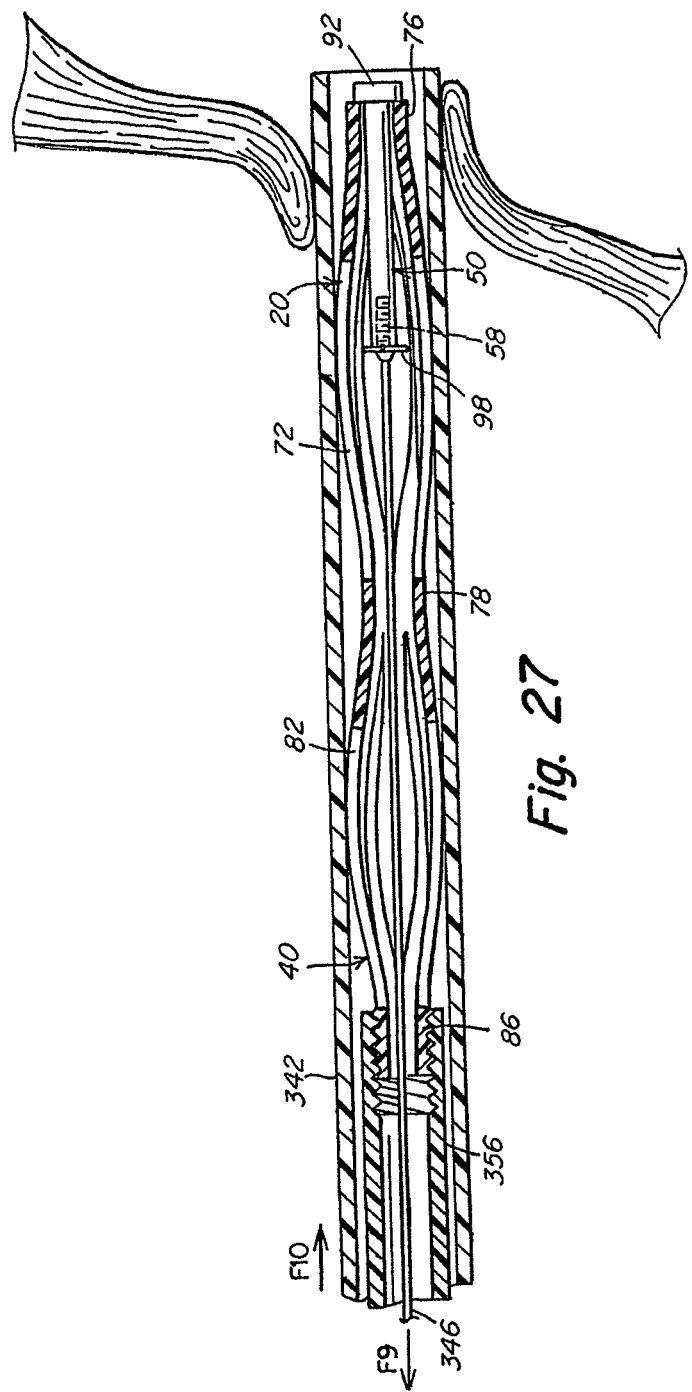
Figure 28:
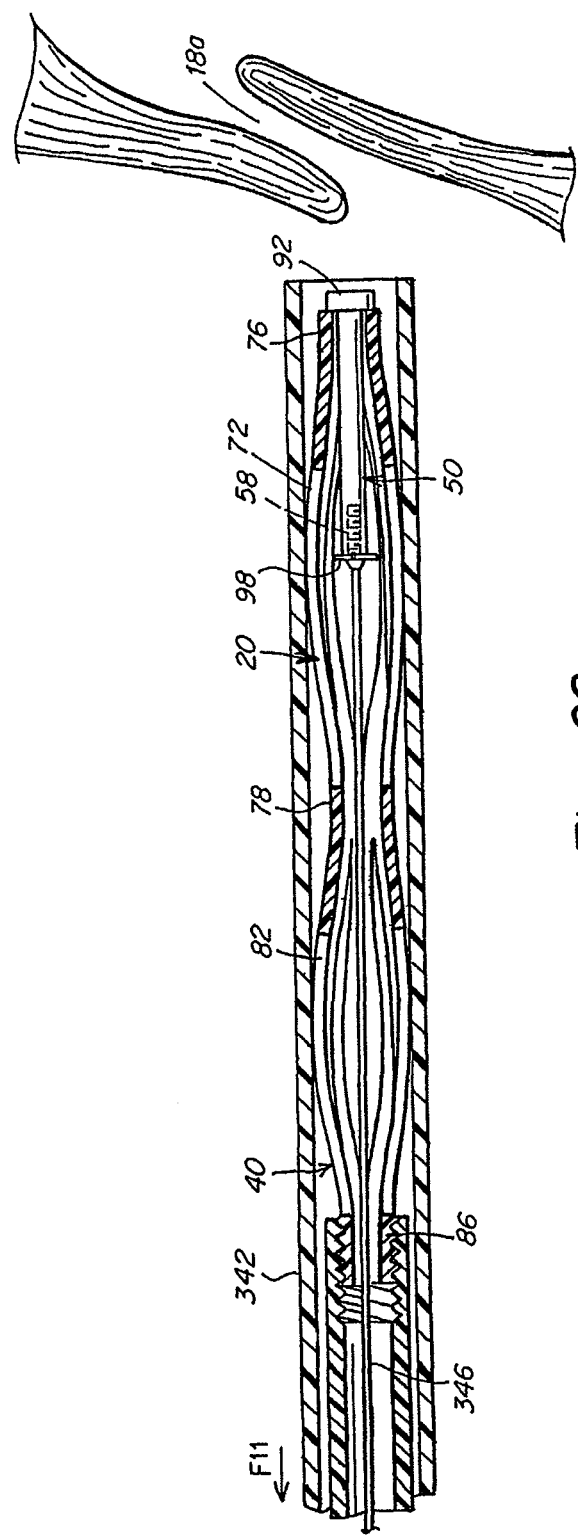

Referring now to FIG. 27, the distal portion 20 of the occluder 70 is fully extended back into it low-profile configuration and forces $F_9$ and $F_{10}$ are applied to the delivery catheter 356 and the delivery sheath 342 in order to retrieve the occluder 70 back into the delivery sheath. Referring to FIG. 28, the delivery sheath 342 and the enclosed occluder 70 are removed from the anatomical aperture 18a and can further be fully removed from the heart 10 by applying force $F_{11}$. This step can also be used as a starting point for redeployment of the occluder 70.

Figure 29:
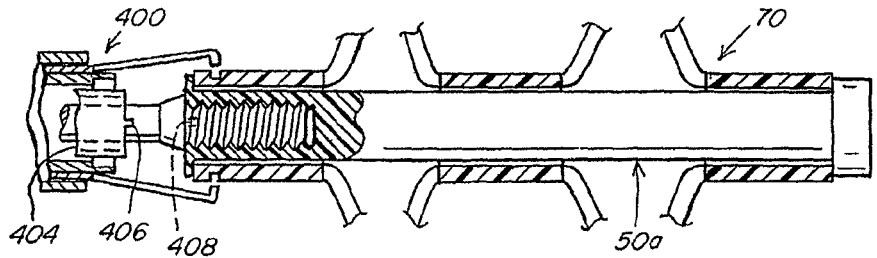
FIG. 29 is a cross-sectional side view of an alternate securement system for the embodiment of the present invention.

FIG. 29 illustrates an alternate embodiment of the invention presently described. FIG. 29 shows a fragmentary view of the catch member 50a engaged with the occluder 70 in a delivery system. In this embodiment, a collet system 400 is used to attach the occluder 70 to the delivery catheter 356. The system is described in more detail in U.S. patent application Ser. No. 11/235,661, which is incorporated by reference herein in its entirety. In this embodiment, the catch member 50a may or may not be fixed to the distal end of the occluder 70. If the catch member 50a is not fixed, a blade and slot system (described above) can be used to secure the catch member in the desired orientation with respect to the occluder. In particular, a delivery catheter 404 includes blades 406 that fit into slots 408 of the catch member 50a. The blade system is particularly advantageous when the distal side of the catch member is able to rotate with respect to the occluder 70. The blades 406 fit within the slots 408 so that the delivery wire 346 can be detached from the catch member 50a.

Figure 31A:
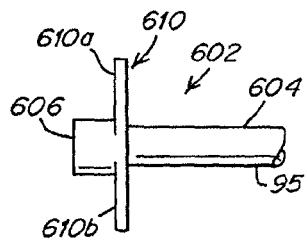
FIGS. 31A and 31B are cross-sectional side views of a portion of an alternate embodiment of a catch member according to an aspect of the invention.
Figure 31B:
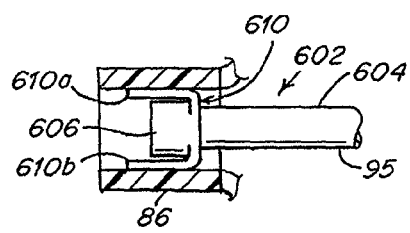

Certain embodiments of the invention incorporate a deformable flap for which the needed deployment force and retrieval force are asymmetric. FIGS. 31A and 31B illustrate a proximal portion 602 of a catch member 50 in accordance with another embodiment of the invention. The proximal portion 602 includes a deformable flap 610, composed of members 610a and 610b, it could also be a single flap member. The portion of the catch member 604 extending distal from the deformable flap 610 has a first diameter (and, respectively, radius), which can be the diameter of the main portion of the catch body 95. The portion of the catch member 606 extending proximal from the deformable flap 610 has a second diameter. The second diameter is greater than the first diameter. In this embodiment, the interference between the proximally bent flap 610 and the axial passage of the occluder 70 during retrieval is greater than the interference between the distally bent flap 610 and the axial passage of the occluder 70 during delivery. This embodiment increases the force required to uncatch the device, particularly relative to the force required to deploy the catch member 50. In an alternative embodiment, other dimensions of the deformable flap 610 can also be adapted to increase the interference and to increase the force required to uncatch the device.

Figure 32A:
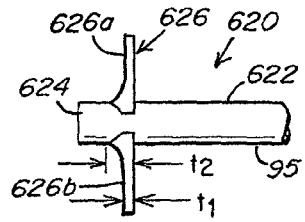
FIGS. 32A and 32B are cross-sectional side views of a portion of an alternate embodiment of a catch member according to an aspect of the invention.
Figure 32B:
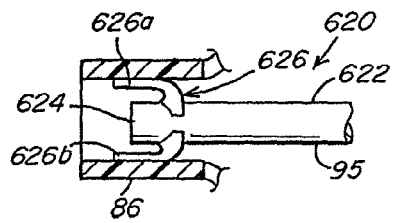

The shape of flap 98 can be altered to make it more difficult to bend proximally and therefore more difficult to uncatch and retrieve. FIGS. 32A and 32B illustrate a proximal portion 620 of a catch member 50 in accordance with another embodiment of the invention. The proximal portion 620 includes a deformable flap 626, composed of members 626a and 626b; flap 626 could also be a single member around the circumference of the catch body in some embodiments. As illustrated in FIG. 32A, the radius of curvature at the junction between the flap 626 and the portion of the catch member 622 extending distal from the flap 626 is smaller than the radius between the flap 626 and the portion of the catch member 622 extending proximal from the flap 626. Thus, in one embodiment, the deformable flap 626 have a first thickness $t_1$ at the outer ends and a second thickness $t_2$, that is greater than $t_1$, at the base where the deformable flap 626 joins the main body of the catch member 50. In one embodiment, the deformable flap 626 is straight on the distal side and curved on the proximal side, particularly at the base. In another embodiment, base of flap 626 has a greater radius on the proximal side than on the distal side. Accordingly, the base of each deformable flap member 626a and 626b is thicker on the proximal side.

Hence, more force is required to bend the flap 626 in the proximal direction, during retrieval of the occluder, than in the distal direction during delivery of the occluder. Accordingly, the force required to deploy and retrieve the occluder 70 are asymmetric and the catch provided by the deformable flap 626 is especially secure, while the ease of deployment is retained. According to alternative embodiment, other changes to the shape of the flap can be made to impart a similar effect.

The embodiments and techniques described here are described preferably for use with a device made of a polymer and formed from a single tube, such that the tube is a single monolithic material or formed with filaments arranged in a tubular structure. The catch mechanism can be all or partly monolithic or integral with the tubular structure, or there can be an absence of any type of bonding or rigid connection to the rest of the tubular structure, in which case there may be some spring force or other force that holds the catch mechanism in place. While the device is thus shown as being substantially formed from a single tubular body, the catch mechanism as described in the embodiments above could be used with other types of devices, including those formed from many pieces, and including devices formed from other materials, including metals, polymers, stainless steel or nitinol.

The term "bioabsorbable," as used in the description above, is also understood to mean "bioresorbable."

In cases in which the device or catch member is made of a polymer, it can be desirable to add an additive or coating to the material to make it radiopaque to make it more visible in a wider variety of imaging techniques.

It will be appreciated that while a particular sequence of steps has been shown and described for purposes of explanation, the sequence may be varied in certain respects, or the steps may be combined, while still obtaining the desired deployment or in some cases to effect deployment in a particular way. For example, the delivery sheath may be advanced or retracted at varying times and in varying degrees, the proximal and distal portions of the occluder may be deployed into the petal configuration in a different sequence, etc. In addition, the steps could be automated.

It will be appreciated that the detailed description of the illustrated embodiments has been provided by way of illustration only and that variations can be made without departing from the scope of the invention, which is indicated by the claims.

What is claimed is:

1. A collapsible medical device for occluding an aperture in a body, the medical device having a first configuration with a reduced profile and a second configuration with an expanded profile, the medical device being adapted to be delivered through a delivery system into a desired delivery location, the medical device comprising:
   an occluder portion having a proximal side having a proximal end and a distal side having a distal end that cooperate to close the defect, and the occluder having a central portion disposed between the proximal side and the distal side, at least one of the proximal and distal sides of the occluder including slits axially formed in a tube to form struts, wherein adjacent slits are axially offset from each other around the circumference of the tube and the struts form petals which rotate in an orthogonal plane relative to the axis of the occluder device when the axial length of the tube is shortened into a deployed state, and wherein at least one strut joined to the central portion forms a portion of two adjacent petals extending from the at least one strut;
   and
   a catch system for holding the medical device in the second configuration, including a catch member having a distal end with a diameter D1 and a proximal end having a diameter D2, wherein D2 is greater than D1, and a flap at the proximal end of the catch member having a base portion of thickness t1 and an outer portion having a thickness t2, wherein t2 is greater than t1; and wherein further the flap is bent distally when the flap is pulled through the proximal end during delivery of the device, wherein the proximal end of the device rests against a distal surface of the flap when the device is in the second configuration and the flap holds the medical device in the second configuration, and wherein further the flap fits inside an interior passage of the occluder portion in during delivery and retrieval, and wherein the flap has a first interference with the interior passage of the occluder portion during delivery and a second interference with the interior passage of the occluder portion during retrieval, and the second interference is greater than the first interference and a first force required to deform the flap for retrieval is greater than a second force required to deform the flap for deployment.

2. The medical device of claim 1, wherein the flap includes two wings.

3. The medical device of claim 2, wherein the circumferential coverage of the wings is separated by cutoff V-shaped notches.

4. The medical device of claim 1, wherein the flap has a rounded shape when viewed axially.

5. The medical device of claim 1, wherein the flap has a rounded surface at the radially outermost edge.

6. The medical device of claim 1, wherein the flap has a thickness to width ratio of about 1 to about 2.

7. The medical device recited in claim 6, wherein the flap has two wings with rounded surfaces at the radially outermost edge.

8. The medical device of claim 1, wherein the proximal end of the catch member comprises threads that secure the catch member to the delivery system.

9. The medical device of claim 1, wherein the occluder portion is bioresorbable.

10. The medical device of claim 1, wherein the occluder portion is nitinol.

* * * * *